United States Patent
Sauzeau et al.

(10) Patent No.: US 11,795,144 B2
(45) Date of Patent: Oct. 24, 2023

(54) INHIBITORS OF RAC1 AND USES THEREOF FOR TREATING CANCERS

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE DE NANTES, Nantes (FR); CHU NANTES, Nantes (FR)

(72) Inventors: Vincent Sauzeau, Bouguenais (FR); Gervaise Loirand, Thouare-sur-Loire (FR); Jacques Lebreton, Nantes (FR); Arnaud Tessier, Orvault (FR); Agnès Quemener, Nantes (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE DE NANTES, Nantes (FR); CHU NANTES, Nantes (FR)

( * ) Notice: Subject to any disclaimer, the term of this patent is extended or adjusted under 35 U.S.C. 154(b) by 136 days.

(21) Appl. No.: 16/619,311

(22) PCT Filed: Jun. 6, 2018

(86) PCT No.: PCT/EP2018/064928
§ 371 (c)(1),
(2) Date: Dec. 4, 2019

(87) PCT Pub. No.: WO2018/224563
PCT Pub. Date: Dec. 13, 2018

(65) Prior Publication Data
US 2020/0095199 A1  Mar. 26, 2020

(30) Foreign Application Priority Data

Jun. 6, 2017 (EP) .................................. 17305664

(51) Int. Cl.
*A61P 35/00* (2006.01)
*C07C 311/29* (2006.01)

(52) U.S. Cl.
CPC ............ *C07C 311/29* (2013.01); *A61P 35/00* (2018.01)

(58) Field of Classification Search
CPC .............................. C07C 311/29; A61P 35/00
See application file for complete search history.

(56) References Cited

U.S. PATENT DOCUMENTS

| | | |
|---|---|---|
| 2,192,490 A | 3/1940 | Warnat |
| 2,407,309 A | 9/1946 | Lott et al. |
| 5,932,599 A | 8/1999 | Boes et al. |
| 6,521,658 B1 | 2/2003 | Li et al. |
| 6,638,921 B1 | 10/2003 | Sauve et al. |
| 2011/0201609 A1 | 8/2011 | Lawrence et al. |

(Continued)

FOREIGN PATENT DOCUMENTS

| | | |
|---|---|---|
| CN | 101 429 142 A | 5/2009 |
| JP | 10193554 A | 7/1998 |

(Continued)

OTHER PUBLICATIONS

Roger S, Gillet L, Le Guennec J-Y and Besson P (2015) Voltage-gated sodium channels and cancer: is excitability their primary role?*
"Treatment." (2009). In Mosby's Dictionary of Medicine, Nursing, & Health Professions. Retrieved from <http://www.credoreference.com/entry/ehsmosbymed/treatment> on Nov. 18, 2010.*
Salum L B, et al, "N-(1'-naphthyl)-3,4,5-trimethoxybenzohydr azide as microtubule destabilizer: Synthesis, cytotoxicity, inhibition of cell migration andin vivoactivity against acute lymphoblastic leukemia", European Journal of Medicinal Chemistry, vol. 96, Feb. 23, 2015, pp. 504-518.

(Continued)

*Primary Examiner* — Alicia L Otton
(74) *Attorney, Agent, or Firm* — WC&F IP

(57) ABSTRACT

The present invention concerns a compound having the following formula (I):

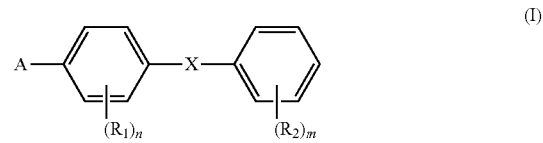

Figure 1:
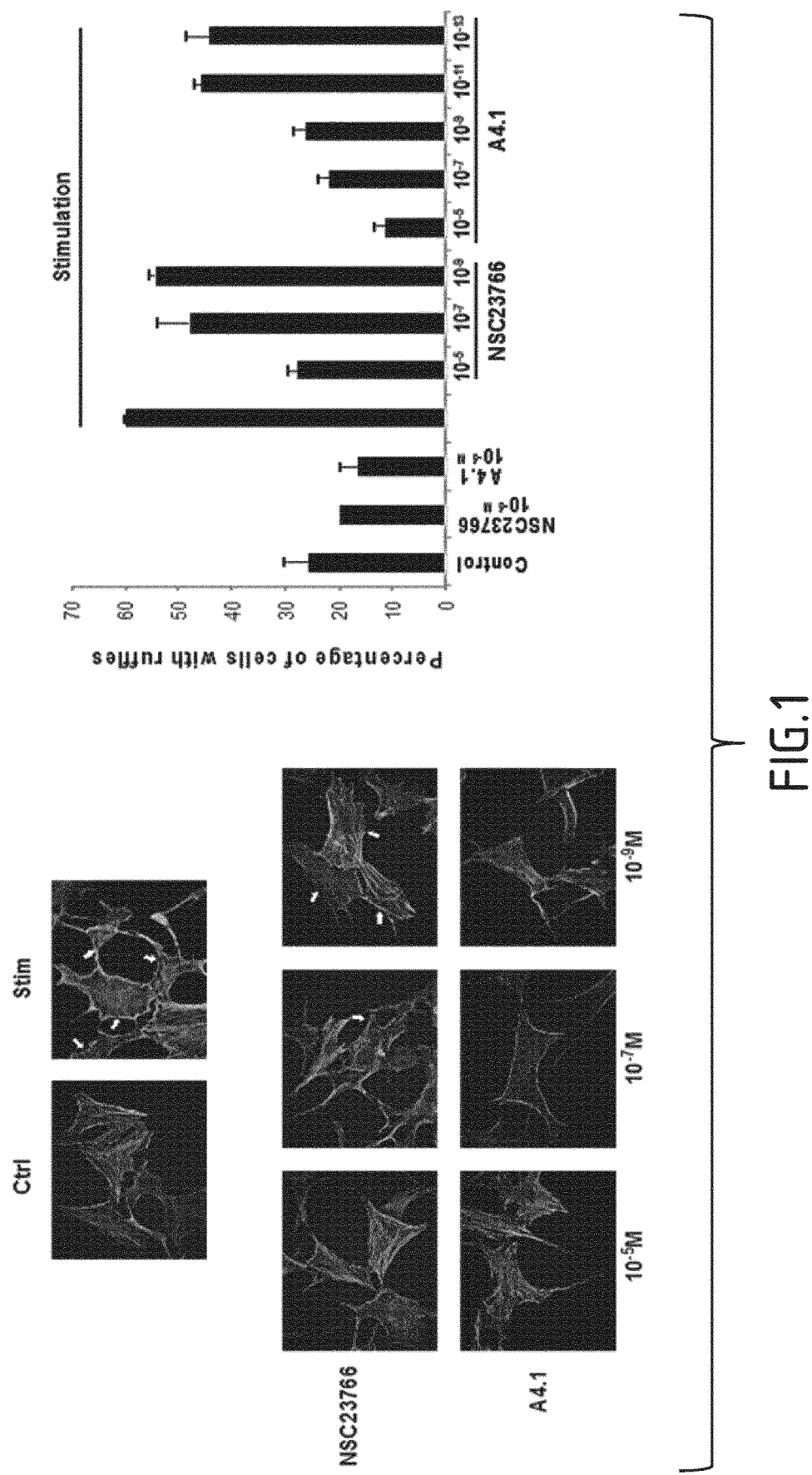

wherein:
A is in particular —N(R'$_a$)—C(=O)—R, R'$_a$ being H or a (C$_1$-C$_6$)alkyl group, and R being preferably a group having the following formula (II):

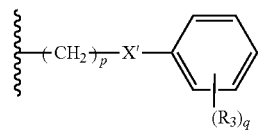

X is in particular chosen from the group consisting of: —SO$_2$—N(R'$_b$)—, R'$_b$ being H or a (C$_1$-C$_6$)alkyl group, —N(R"$_b$)—SO$_2$—, R"$_b$ being H or a (C$_1$-C$_6$) alkyl group, —CO—NH—, and —NH—CO—,
for use for the treatment of cancers, such as metastatic cancers.

4 Claims, 9 Drawing Sheets

(56) References Cited

U.S. PATENT DOCUMENTS

| | | | |
|---|---|---|---|
| 2011/0275635 A1* | 11/2011 | Brouillette | A61P 31/00 564/49 |
| 2012/0100609 A1* | 4/2012 | Crawford | A61P 31/00 435/375 |

FOREIGN PATENT DOCUMENTS

| | | |
|---|---|---|
| JP | 2006508906 A | 3/2006 |
| JP | 2011032294 A | 2/2011 |
| WO | 2004/005278 A1 | 1/2004 |
| WO | 2005013914 A1 | 2/2005 |
| WO | 2012/142698 A1 | 10/2012 |
| WO | 2013/009799 A1 | 1/2013 |
| WO | 2013009799 A1 | 1/2013 |
| WO | 2015/138377 A1 | 9/2015 |

OTHER PUBLICATIONS

A. Natarajan et al, "Novel arylsulfoanilide-oxindole hybrid as an anticancer agent that inhibits translation initiation", Journal of Mediciinal Chemistry, vol. 47, No. 21, Oct. 7, 2004, pp. 4979-4982.

Munikumar Reddy Doddareddy et al, "Hologram quantitative structure activity relationship studies on 5-HT6 antagonists", Bioorganic & Medicinal Chemistry, vol. 12, No. 14, Jul. 1, 2004, pp. 3815-3824.

Ivan M. Kompis et al, "DNA and RNA Synthesis: Antifolates", Chemical Reviews, vol. 105, No. 2, Feb. 1, 2005, pp. 593-620.

Zheng et al, "Analgesic agents without gastric damage: Design and synthesis of structurally simple benzenesulfonanilide-type cyclooxygenase-1-selective inhibitors", Bioorganic & Medicinal Chemi, vol. 15, No. 2, Dec. 12, 2006, pp. 1014-1021, Pergamon, GB.

Zheng et al, "Corrigendum to 'Analgesic Design and synthesis of structurally simple benzenesulfonanilide-type cyclooxygenase-1-selective inhibitors' [Bioorg. Med. Chem. 15 (2007) 1014-1021]", Bioorganic & Medicinal Chemistry, vol. 15, No. 9, Mar. 29, 2007, pp. 3299-3300, Pergamon, GB.

Database Caplus [Online] Chemical Abstracts Service, Columbus, OH, US: Jan. 1, 2012, Y. Shenghui et al.: "Nitrogen-containing polyhydroxylated aromatics as HIV-1 integrase inhibitors.".

Perlovich German L et al: "Thermodynamic aspects of solubility and partitioning processes of some sulfonamides in the solvents modeling biological media", Journal of Chemical Thermodynamics, vol. 69, Oct. 3, 2013, pp. 56-65.

Lawrence H R et al, "Synthesis and biological evaluation of naphthoquinone analogs as a novel class of proteasome inhibitors", Bioorganic & Medicinal Chemistry, vol. 18, No. 15, Aug. 1, 2010, pp. 5576-5592, Pergamon, GB.

V Masevicius et al, "4-amino-5-(arylaminomethyl)-2-(methylthio)furo[2,3-d]pyrimidine with N-Mesyl and N-Nosylarylamines", Synthesis, vol. 44, Mar. 27, 2012, pp. 1329-1338.

Database Registry [Online] Chemical Abstracts Service, Columbus, OH, US: Nov. 11, 2007, Ambinter: "4-amino-N-(2,4-dimethoxyphenyl)-benzensul fonamide.".

Database Registry [Online] Chemical Abstracts Service, Columbus, OH, US: Jul. 15, 2004, Labotest: "N-(3,4-dimethoxyphenyl)-4-nitro-benzenesulfonamide.".

Database Registry [Online] Chemical Abstracts Service, Columbus, OH, US: Jun. 3, 2002, ChemBridge Corporation: "N-(3,4-dimethoxyphenyl)-4-nitro-benzenesulfonamide.".

Database Registry [Online] Chemical Abstracts Service, Columbus, OH, US: Apr. 23, 2008, Ambinter: "4-amino-N-(3methylthio-phenyl)-benzenesulfonamide.".

Database Registry [Online] Chemical Abstracts Service, Columbus, OH, US: Sep. 24, 1998, "4-amino-N-(3methylthio-phenyl)-benzenesulfonamide.".

Acetamide; Jun. 10, 2003; Chemical Library Supplier: Ambinter; 528580-84-9.

Propanamide; Jan. 29, 2004; Chemical Library Supplier: Ambinter; 642998-77-4.

Carbamic Acid; Jul. 22, 2007; Chemical Library Supplier: ZereneX Molecular Limited; 943082-65-3.

Benzenesulfonamide; Nov. 11, 2007; Chemical Library Supplier: Ambinter; 952946-68-8.

Propanamide; Jun. 17, 2004; Chemical Library Supplier: ChemBridge Corporation; 694515-65-6.

Benzenesulfonamide; Apr. 13, 2001; CAS Client Services; 331240-24-5.

"Highly specific N-monomethylation of primary aromatic amines", Tetrahedron 62, Apr. 27, 2006.

Viktoras Masevicius et al., "4-Amino-5-(arylaminomethyl)-2-(methylthio)furol2,3-dlpyrimidines via Mitsunobu Reaction of 4-Amino-5-(hydroxymethyl)-2-(methylthio)furo-[2,3,-dlpyramidine with N-Mesyl- and N-Nosylarylamines", Synthesis 44, 2012.

Chemical Library 642998-77-4, Jan. 29, 2004.

Chemical Library 694515-65-6, Jun. 17, 2004.

* cited by examiner

INHIBITORS OF RAC1 AND USES THEREOF FOR TREATING CANCERS

The present invention concerns new inhibitors of RAC1, as well as pharmaceutical compositions comprising said inhibitors. The present invention also concerns said compounds for use for treating cancers, in particular metastatic cancers.

The Ras-related small GTPase member of the Rho family, Rac1, is a binary molecular switch, cycling between an inactive GDP-bound "OFF" state and an active GTP-bound "ON" state to regulate essential cellular functions including NADPH oxidase activity, actin cytoskeleton organization, and modulation of gene expression. When this activation/inactivation cycling is compromised, Rac1 activity is implicated in various steps of oncogenesis including initiation, progression, invasion, and metastasis. Overexpression of Rac1 has been reported in colorectal, pancreatic, breast, and testicular cancers and in various leukemias. Moreover, aberrant activation of upstream regulators of Rac1, such as the Rac exchange factors TIAM1, PREX1, and ECT2, have been implicated in various cancers. Recently, the discovery of a hotspot mutation in RAC1 (c.85C>T) in up to 9% of sun-exposed melanomas identified Rac1 as a new actor of melanoma genesis. The RAC1 c.85C>T mutation and the resulting substitution of proline at position 29 with serine confers constitutive activity to Rac1 protein mutant [Rac1(P29S)], which is a driver of melanoma formation. Indeed, the RAC1(P29S) mutation is the third most recurrent mutation in melanoma after BRAFV600 and NRASQ61. There is also emerging evidence that Rac may be mutationally activated in other forms of cancer. For example, the RAC1(P29S) mutation has been reported in a head and neck tumor as well as a breast tumor. Other transforming RAC mutations [Rac1(N921), Rac1(C157Y), Rac2(P29L), and Rac2(P29Q)] have also been found in human cancer cell lines, but the RAC1P29S is the most common cancer-associated recurrent missense mutation in a Rho family GTPase. Targeted depletion of Rac1 reduced the rate of cell proliferation of Rac1(P29S) mutant melanoma, as well as Rac1 wild-type melanoma cell proliferation and invasion, suggesting that Rac1 blockade may have therapeutic value in repressing tumor progression and metastasis.

However, the currently available drugs that inhibit Rac1 (EHT 1864 and NSC23766) are not efficient at inhibiting Rac1(P29S) mutant and induce critical off-target effects, thus highlighting the obvious need to discover new Rac inhibitors.

There is thus a need to find efficient Rac inhibitors in order to efficiently treat cancers, such as metastatic cancers.

The aim of the present invention is thus to provide new inhibitors of RAC1.

Another aim of the invention is to provide new compounds efficient for treating cancers, and especially for treating metastatic cancers.

Another aim of the invention is to provide RAC1 inhibitors useful for treating cancers.

Thus, the present invention relates to a compound having the following formula (I):

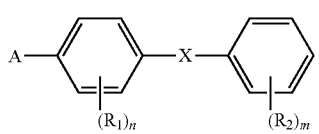
(I)

wherein:
A is chosen from the group consisting of:
—NR$_a$R$_b$, R$_a$ and R$_b$, identical or different, being H or a (C$_1$-C$_6$)alkyl group, and preferably NH$_2$,
—NO$_2$,
—N(CO—R$_c$)(CO—R'$_c$), R$_c$ and R'$_c$, identical or different, representing a (C$_2$-C$_6$)alkenyl group, or forming together with the carbon atoms carrying them and the nitrogen atom a heterocycloalkyl group comprising 5 to 10 atoms, and
—N(R'$_a$)—C(=O)—R, and

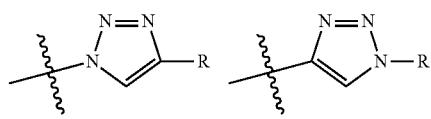

wherein:
R'$_a$ is H or a (C$_1$-C$_6$)alkyl group, optionally substituted by at least one halogen atom, R'$_a$ being preferably H;
R is chosen from the group consisting of:
(C$_1$-C$_6$)alkyl groups, optionally substituted, for example by a halogen atom,
(C$_2$-C$_6$)alkenyl groups,
(C$_2$-C$_6$)alkynyl groups, optionally substituted by a group —SiR$_e$R$_f$R$_g$, R$_e$, R$_f$, and R$_g$ being, independently from each other, chosen from (C$_1$-C$_6$)alkyl groups, and
groups having the following formula (II):

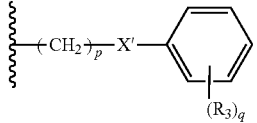

wherein:
p is an integer comprised between 1 and 3,
X' is chosen from the group consisting of:
—S—, —O—, —NH—, —NR$_d$—, —CH$_2$—, —SO$_2$—, and —SO—, R$_d$ being H or a (C$_1$-C$_6$)alkyl group;
q is 0 or is an integer comprised between 1 and 5,
the R$_3$ groups, identical or different, are chosen from the group consisting of: (C$_1$-C$_6$)alkyl groups, halogen atoms, (C$_1$-C$_6$)alxoxy groups, (C$_1$-C$_6$)thioalkyl groups, and —NR$_a$R$_b$ groups, R$_a$ and R$_b$, identical or different, being H or a (C$_1$-C$_6$)alkyl group, and preferably —NH$_2$;
—CH$_2$—C(=O)—R, wherein R is as defined above;
—N(R'$_a$)—SO$_2$—R, wherein R and R'$^a$ are as defined above, R'$^a$ being preferably H;
—N(R'$_a$)—C(=O)—OR, wherein R and R'$^a$ are as defined above, R'$^a$ being preferably H;
—N(R'$_a$)—C(=O)—N(R'$_a$)—R, wherein R and R'$^a$ are as defined above, R'$^a$ being preferably H;
—N(R'$_a$)—SO$_2$—N(R'$_a$)—R, wherein R and R'$^a$ are as defined above, R'$^a$ being preferably H;
X is chosen from the group consisting of:
—SO$_2$—N(R'$_b$)—, R'$_b$ being H, a (C$_1$-C$_6$)alkyl group or a —C(=O)—CH=CH$_2$ group, —N(R"$_b$)—SO$_2$—, R"$_b$ being H or a (C$_1$-C$_6$) alkyl group,
—CO—NH—, —NH—CO—,
—NH—CO—NH—,
—NH—SO$_2$—NH—,
—NH—CO—O—,
—CO—O—,
—HC═CH—,
—C≡C—,

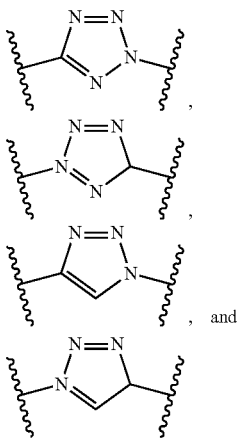, and n is 0 or is an integer comprised between 1 and 4,
the R$_1$ groups, identical or different, are chosen from the group consisting of: halogen atoms, (C$_1$-C$_6$)alkyl groups, (C$_1$-C$_6$)alxoxy groups, (C$_1$-C$_6$)thioalkyl groups, —SCF$_3$, —SF$_5$, and —NR$_a$R$_b$ groups, R$_a$ and R$_b$, identical or different, being H or a (C$_1$-C$_6$)alkyl group, and preferably —NH$_2$;
m is 0 or is an integer comprised between 1 and 5,
the R$_2$ groups, identical or different, are chosen from the group consisting of: halogen atoms, (C$_1$-C$_6$)alkyl groups, (C$_1$-C$_6$)alkoxy groups, (C$_1$-C$_6$)thioalkyl groups, —SCF$_3$, —SF$_5$, and —NR$_a$R$_b$ groups, R$_a$ and R$_b$, identical or different, being H or a (C$_1$-C$_6$)alkyl group, and preferably —NH$_2$;
for use for the treatment of cancers, in particular metastatic cancers.

The present invention is thus based on the activity of inhibition of RAC1 of the compounds of formula (I).

According to the invention, as cancers, one may cite: colorectal cancer, pancreatic cancer, breast cancer, testicular cancer, leukemias, head and neck tumor, or melanoma.

According to a preferred embodiment, the present invention relates to a compound of formula (I) as defined above, for the treatment of breast cancer.

In the context of the present invention, the expression "C$_t$-C$_z$ ( . . . )" means a carbon-based chain which can have from t to z carbon atoms, for example C$_1$-C$_6$ means a carbon-based chain which can have from 1 to 6 carbon atoms.

Within the present application, the term "alkyl group" means: a linear or branched, saturated, hydrocarbon-based aliphatic group comprising, unless otherwise mentioned, from 1 to 6 carbon atoms. By way of examples, mention may be made of methyl, ethyl, n-propyl, isopropyl, butyl, isobutyl, tert-butyl or pentyl groups.

Within the invention, the term "alkenyl group" includes partially unsaturated, nonaromatic, hydrocarbon groups comprising, unless otherwise mentioned, from 2 to 6 carbon atoms.

Within the invention, the term "alkynyl group" means a nonaromatic, hydrocarbon group comprising at least one triple bond, and comprising, unless otherwise mentioned, from 2 to 6 carbon atoms.

Within the present invention, the term "heterocycloalkyl group" means: a 5-to 10-membered, saturated or partially unsaturated, monocyclic or bicyclic group comprising from one to three heteroatoms selected from O, S or N.

Within the present invention, the term "alkoxy group" means: an —O-alkyl radical where the alkyl group is as previously defined. By way of examples, mention may be made of —O—(C$_1$-C$_4$)alkyl groups, and in particular the —O-methyl group, the —O-ethyl group as —O—C$_3$alkyl group, the —O-propyl group, the —O-isopropyl group, and as —O—C$_4$alkyl group, the —O-butyl, —O-isobutyl or —O-tert-butyl group;

Within the present invention, the term "halogen atom" means: a fluorine, a chlorine, a bromine or an iodine.

According to an embodiment, when X is —HC═CH—, then this double bond may be cis or trans.

According to an embodiment, in formula (I), when A represents a group —N(CO—R$_c$)(CO—R'$_c$), R$_c$ and R'$_c$, identical or different, represent a (C$_2$-C$_6$)alkenyl group. Preferably, A represents a group —N(CO—CH═CH$_2$)$_2$.

According to another embodiment, in formula (I), when A represents a group —N(CO—R$_c$)(CO—R'$_c$), R$_c$ and R'$_c$, identical or different, form together with the carbon atoms carrying them and the nitrogen atom a heterocycloalkyl group comprising 5 to 10 atoms. According to this embodiment, A may thus represent a group derived from maleimide or phtalimide.

According to an embodiment, in formula (I), when A represents a group —N(R'$_a$)—C(═O)—R, R'$_a$ is preferably H. According to this embodiment, R is preferably a group of formula (II) as defined above. Preferably, in formula (II), X' is —S—, —O— or —CH$_2$—, and is more preferably —S—.

Preferably, in formula (II), q is 0, 1 or 2.

Preferably, in formula (II), R$_3$ is an alkyl group such as methyl, especially p-Me.

According to a preferred embodiment, in formula (I), A is preferably chosen from the group consisting of: —NH$_2$, —NO$_2$, —N(CO—CH═CH$_2$)$_2$, and —N(R'$_a$)—C(═O)—R, R'$_a$ and R being as defined above.

According to a preferred embodiment, in formula (I), A is preferably chosen from the group consisting of: —NH$_2$, —NO$_2$, —N(CO—CH═CH$_2$)$_2$, and —NH—C(═O)—R, R being as defined above.

A preferred subgroup of compounds used according to the invention is constituted by compounds having the following formula (III):

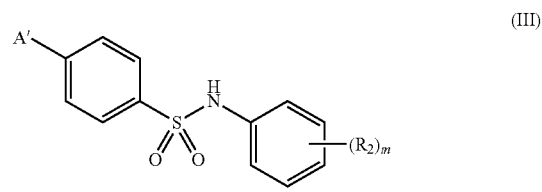

(III)

wherein:

A' is NO$_2$ or NH$_2$; and m and R$_2$ are as defined above in formula (I).

The compounds of formula (III) correspond to compounds of formula (I) as defined above wherein A is NO$_2$ or NH$_2$, n=0, and X is —SO$_2$—NH—.

Preferably, in formula (III), m is 1 or 2.

Preferably, in formula (III), the R$_2$ groups, which may be identical or different, are chosen from alkoxy groups.

According to an embodiment, in formula (III), R$_2$ is a methoxy group. Preferably, when m=1, R$_2$ is a methoxy group in ortho or meta position. Preferably, when m=2, the R$_2$ groups are methoxy groups in 2- and 5-positions.

Another preferred subgroup of compounds used according to the invention is constituted by compounds having the following formula (IV):

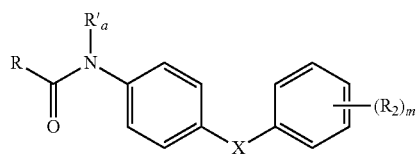
(IV)

wherein R, R'$_a$, X, m, and R$_2$ are as defined above in formula (I).

The compounds of formula (IV) correspond to compounds of formula (I) as defined above wherein A is —N(R'$_a$)—C(=O)—R, and n=0.

According to an embodiment, in formula (IV), R'$_a$ is H. According to an embodiment, in formula (IV), R is a group of formula (II) as defined above. Preferably, in formula (II), X' is —S—, —O— or —CH$_2$—, and is more preferably —S—. Preferably, in formula (II), q is 0, 1 or 2. Preferably, in formula (II), R$_3$ is an alkyl group such as methyl, especially p-Me.

Another preferred subgroup of compounds used according to the invention is constituted by compounds having the following formula (V):

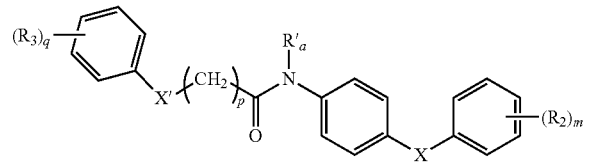
(V)

wherein R'$_a$, X, X', p, q, m, R$_2$ and R$_3$ are as defined above in formula (I).

The compounds of formula (V) correspond to compounds of formula (IV) as defined above wherein R is a group of formula (II) as defined above.

According to an embodiment, in formula (V), R'$_a$ is H. Preferably, for compounds of formula (V), X' is —S—, —O— or —CH$_2$—, and is more preferably —S—.

Preferably, in formula (V), q is 0, 1 or 2.

Preferably, in formula (V), R$_3$ is an alkyl group such as methyl, especially p-Me.

Preferably, in formula (V), m is 1 or 2, and the R$_2$ groups are chosen from the alkyl and alkoxy groups.

Another preferred subgroup of compounds used according to the invention is constituted by compounds having the following formula (VI):

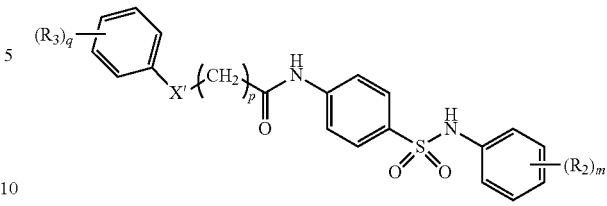
(VI)

wherein X', p, q, m, R$_2$ and R$_3$ are as defined above in formula (I).

The compounds of formula (VI) correspond to compounds of formula (V) as defined above wherein R'$_a$ is H and X is —SO$_2$—NH—.

Preferably, in formula (VI), q=0 or 1, and the R$_3$ groups are chosen from the alkyl groups as defined above.

Preferably, in formula (VI), X' is —CH$_2$— or —S—.

Preferably, in formula (VI), m=1 or 2, and the R$_2$ groups are chosen from the alkyl and alkoxy groups as defined above.

Another preferred subgroup of compounds used according to the invention is constituted by compounds having the following formula (VII):

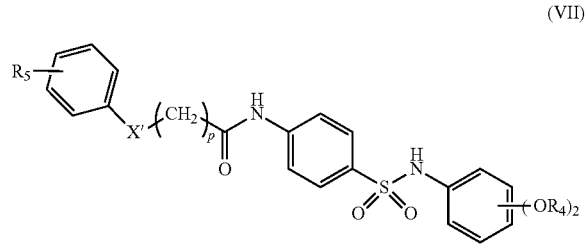
(VII)

wherein:

X' and p are as defined above in formula (I);

R$_5$ is a (C$_1$-C$_6$)alkyl group; and the R$_4$ groups, identical or different, are chosen from the (C$_1$-C$_6$)alkyl groups.

Preferably, in formula (VII), X' is —CH$_2$— or —S—.

The present invention also relates to the compounds having the following formula (I) as defined above as such. It also relates to the compounds having one of the formulae (III), (IV), (V), (VI), and (VII) as such, said formulae being as defined above.

As preferred compounds used according to the invention, one may mention the followings:

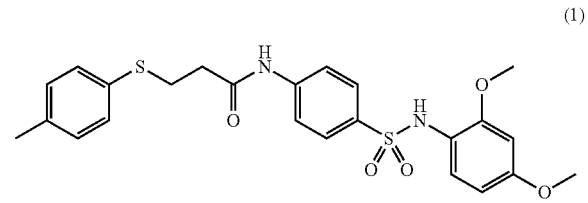
(1)

(2)
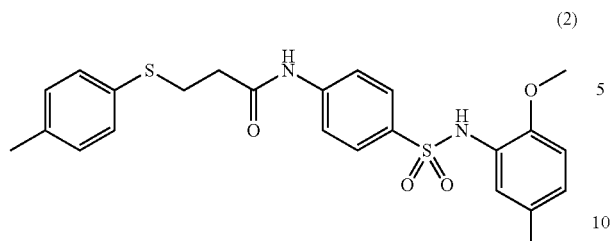
(3)
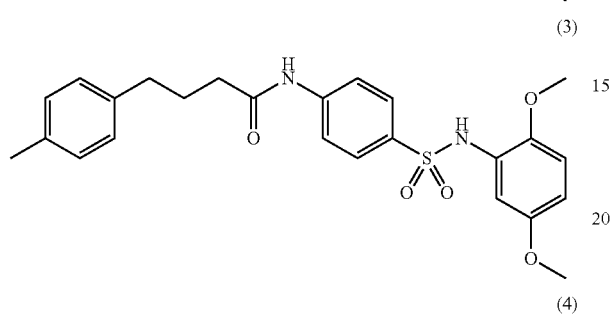
(4)
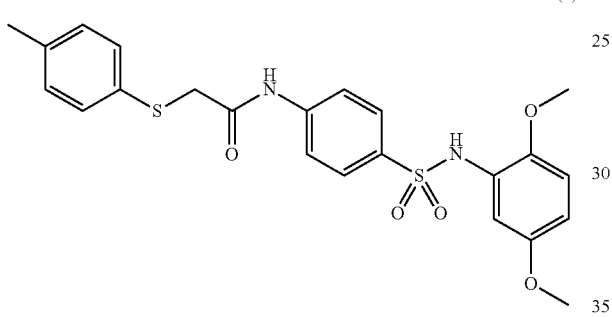
(5)
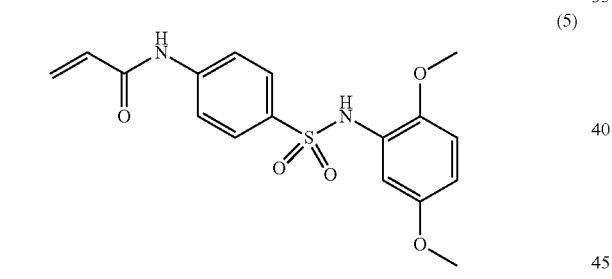
(6)
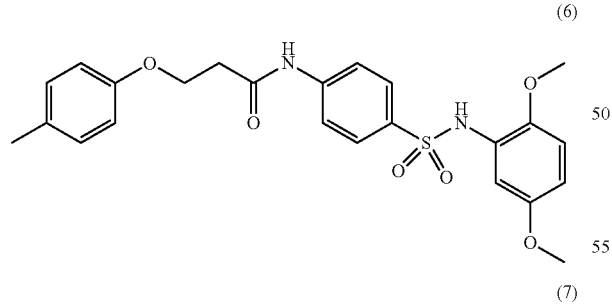
(7)
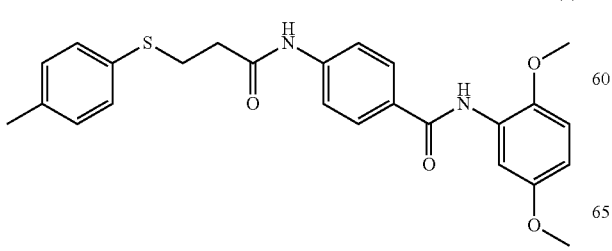
(8)
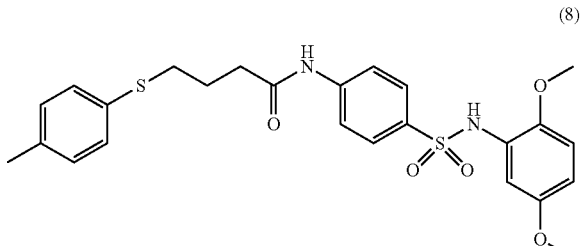
(9)
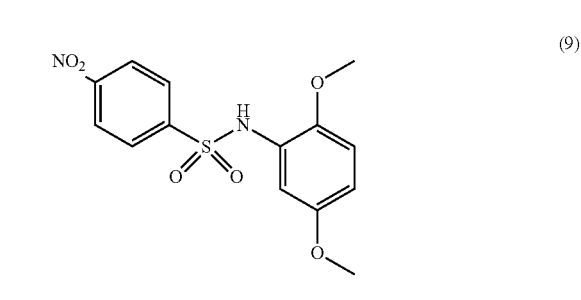
(10)
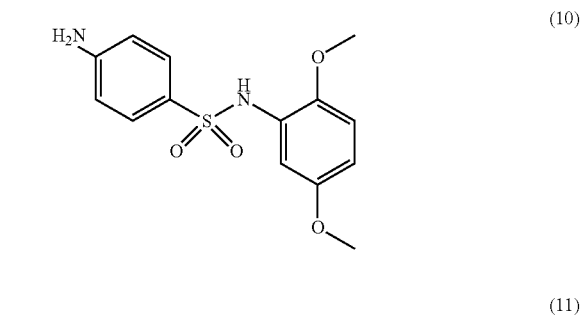
(11)
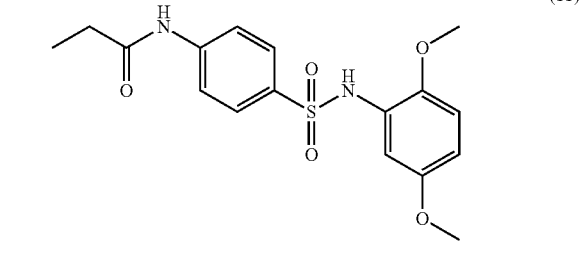
(12)
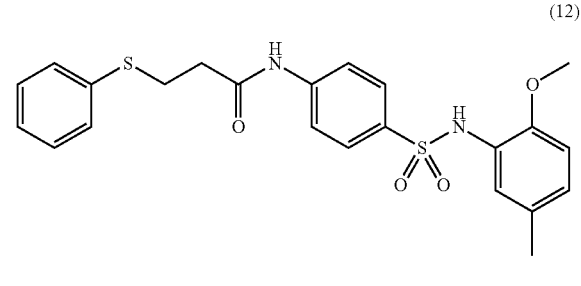
(13)
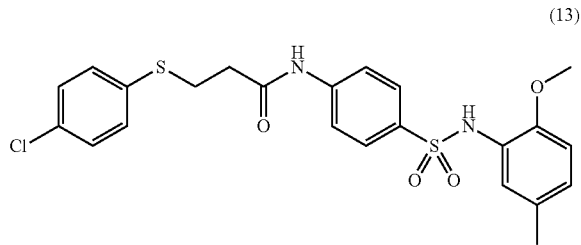

(14)
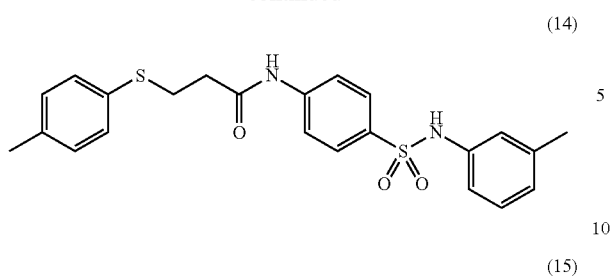
(15)
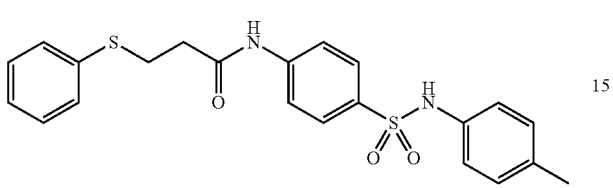
(16)
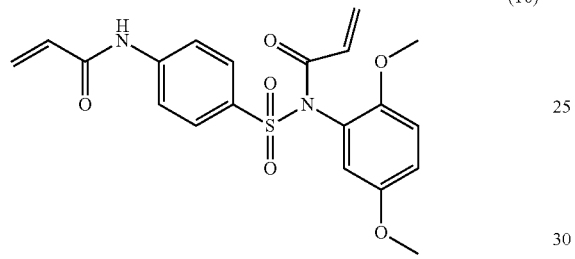
(17)
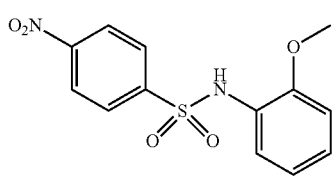
(18)
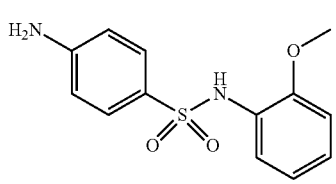
(19)
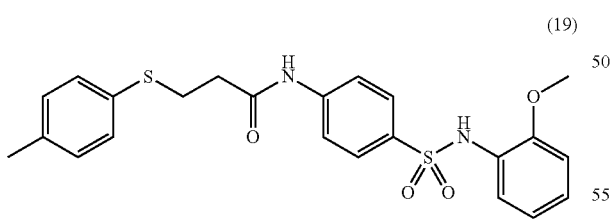
(20)
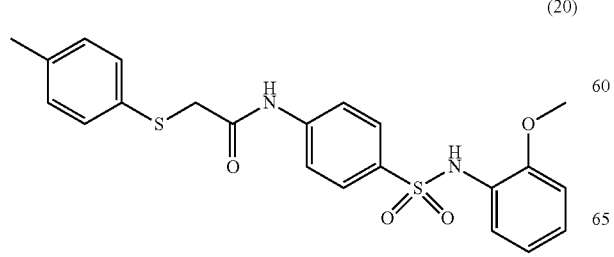
(21)
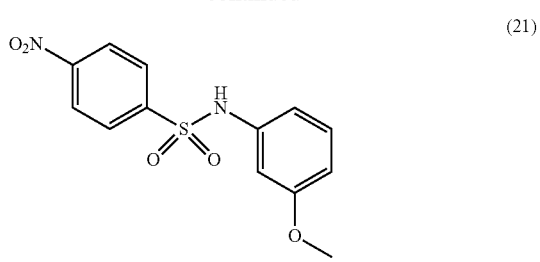
(22)
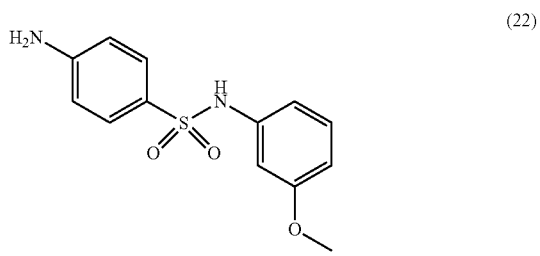
(23)
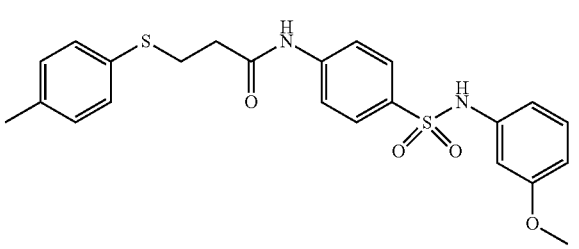
(24)
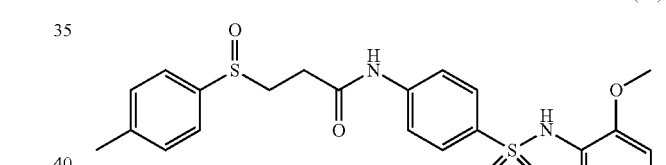
(25)
(26)
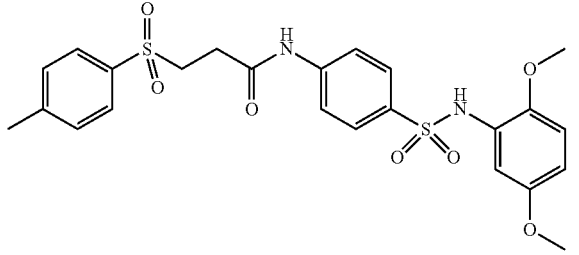
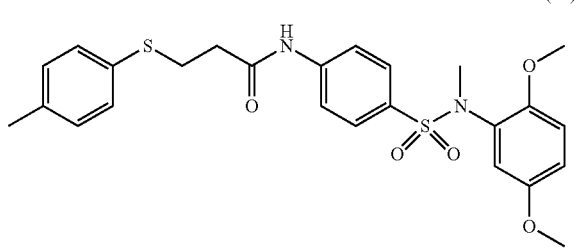

-continued

(27) 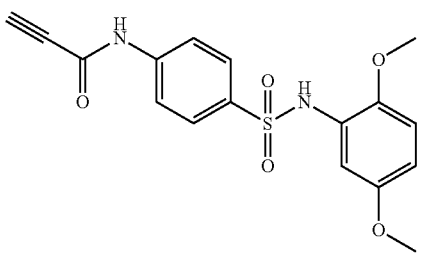

(28) 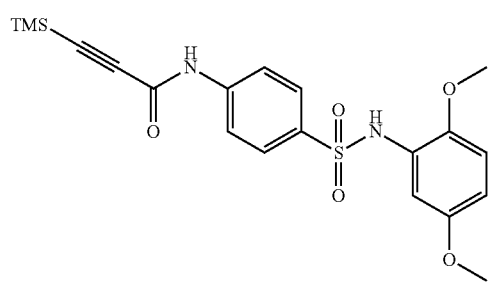

(29) 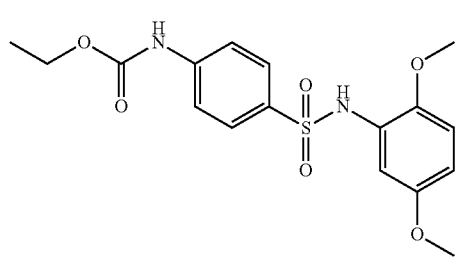

(30) 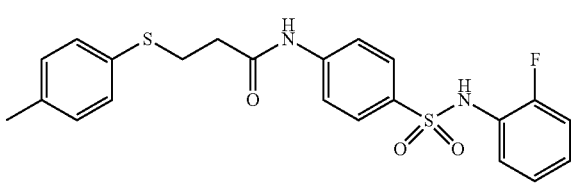

(31) 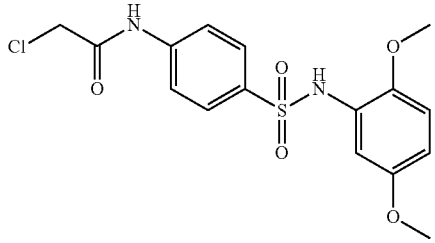

As preferred compounds as such, one may mention the followings: (3), (4), (5), (6), (7), (8), (9), (10), (11), (16), (17), (18), (19), (20), (21), (22), (23), (24), (25), (26), (27), (28), (29), (30), and (31).

The present invention also relates to a medicament comprising a compound as defined above, in particular a compound having one of the formulae (I), (III), (IV), (V), (VI) or (VII).

The present invention also relates to a pharmaceutical composition, comprising a compound as defined above, in particular a compound having one of the formulae (I), (III), (IV), (V), (VI) or (VII), and at least one pharmaceutically acceptable excipient.

These pharmaceutical compositions contain an effective dose of at least one compound according to the invention, or a pharmaceutically acceptable salt, and also at least one pharmaceutically acceptable excipient.

Said excipients are selected, according to the pharmaceutical form and the mode of administration desired, from the usual excipients which are known to those skilled in the art.

EXAMPLES

Preparation of Compounds of Formula (I)

One embodiment of the present invention relates to sulfonamides compounds represented by the following schemes.

As representative examples of these series, the synthesis of sulfonamides derivatives proceeds toward the functionalization of various terminal aniline compounds as shown in scheme 1. The sulfonamide was introduced by reaction of primary aniline with the appropriate p-nitrobenzenesulfonyl chloride under basic conditions as shown in scheme 1. Further reduction of the nitro group in presence of iron gives access to anilines bearing the sulfonamide moieties. Then, finally, the acylation of the resulting primary aniline with the appropriate acyl chloride affords the expected derivatives similar to one of those depicted in formula (VI).

Scheme 1

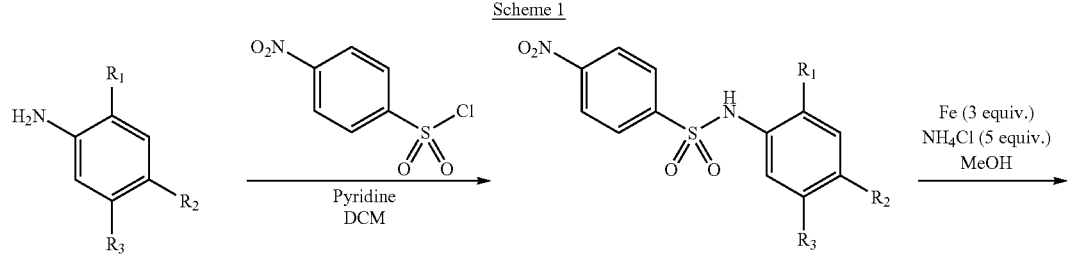

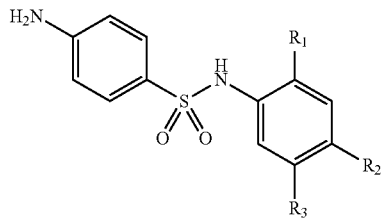

(10) $R_1$ = OMe; $R_2$ = H; $R_3$ = OMe
(19) $R_1$ = OMe; $R_2$ = H; $R_3$ = H
(22) $R_1$ = H; $R_2$ = H; $R_3$ = OMe

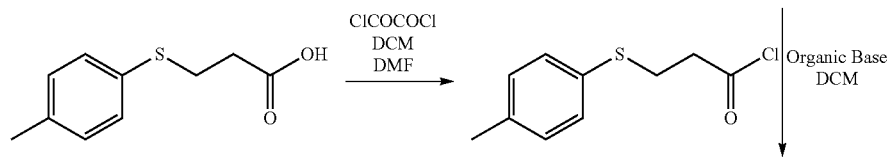

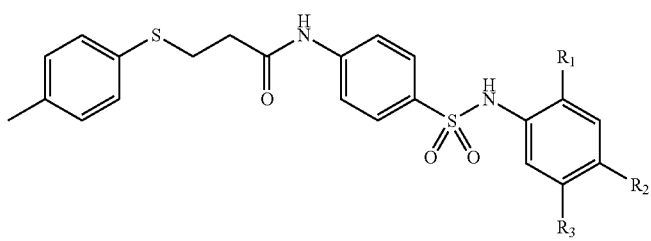

(1) $R_1$ = OMe; $R_2$ = OMe; $R_3$ = H
(2) $R_1$ = OMe; $R_2$ = H; $R_3$ = OMe
(19) $R_1$ = OMe; $R_2$ = H; $R_3$ = H
(23) $R_1$ = H; $R_2$ = H; $R_3$ = OMe
(30) $R_1$ = F; $R_2$ = H; $R_3$ = H

Another embodiment of the present invention relates to another subgroup of compounds featuring varied functional groups of the terminal amides of the sulfonamides. Scheme 2 shows representative examples of these modifications. The synthesis starts from substituted primary anilines (as shown for instance with compound (10) in scheme 2) that are previously obtained via the formation of sulfonamides. The acylation reaction is performed under basic conditions in presence of various acyl chlorides derivatives.

Scheme 2

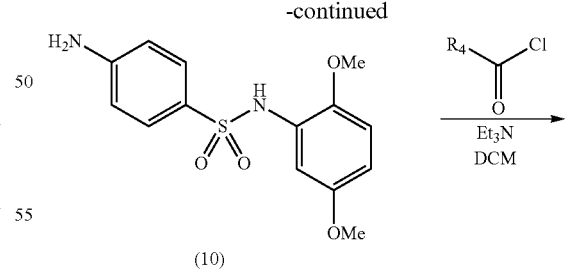

-continued

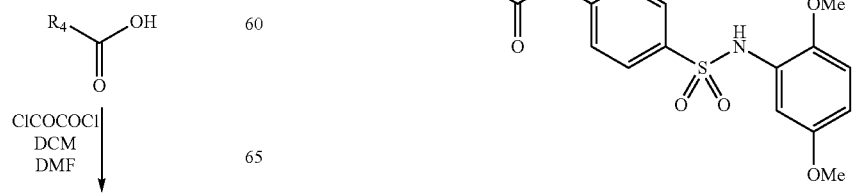

15
-continued
R₄ = 
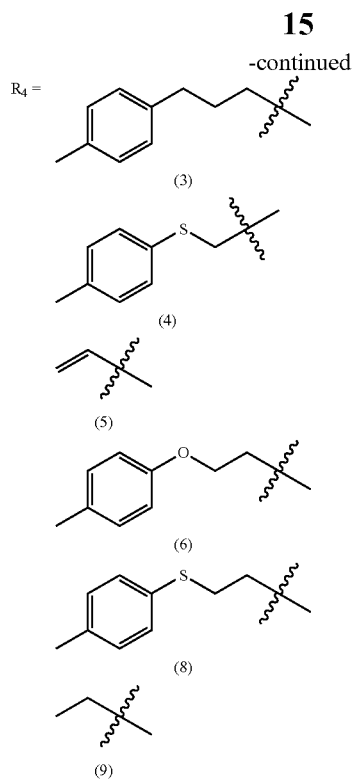
16
-continued
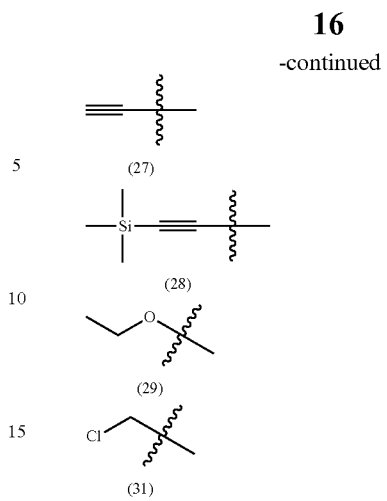
Scheme 3 shows another embodiment of the invention relating to amide compounds, instead of sulfonamide compounds, represented by the following example affording the compound (7).
Scheme 3
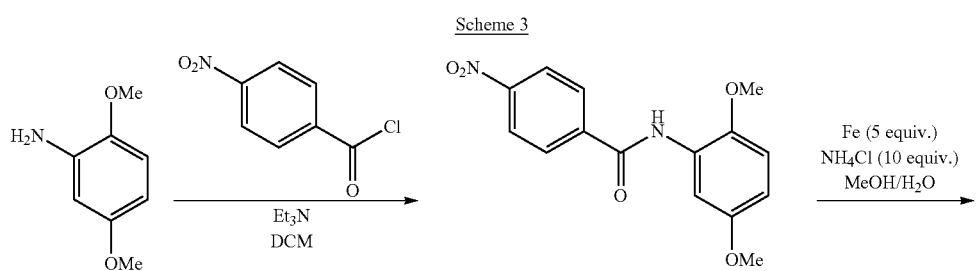
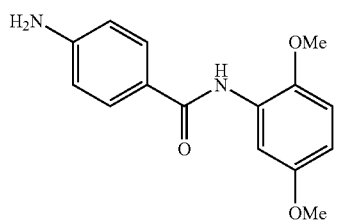
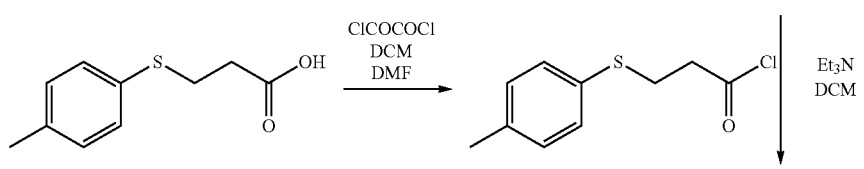

-continued

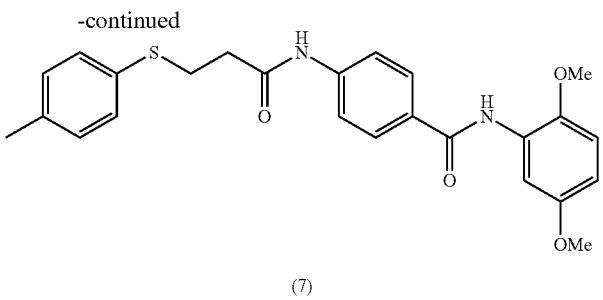

(7)

Scheme 4 shows the synthesis of an example of sulfonamide derivative combining variations of the initial aromatic ring of compound (2) and modification of its initial acylating reagent. This synthesis involves the acylation of the primary aniline under standard conditions.

Scheme 4

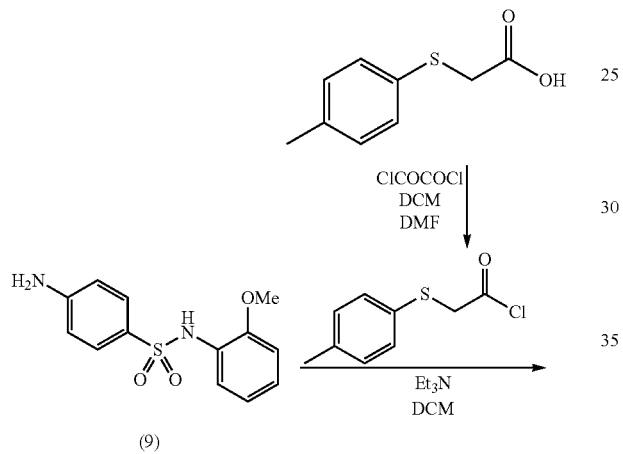

-continued

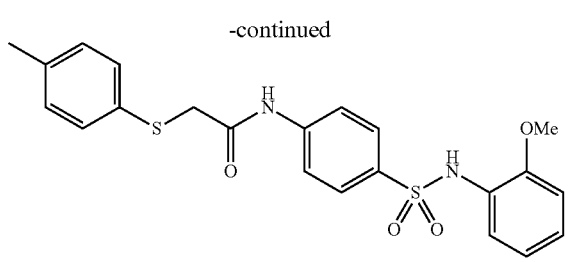

(20)

Scheme 5 and Scheme 6 show representative examples for the synthesis of sulfoxides and sulfones compounds arising from the original sulfonamides subgroup Scheme 5

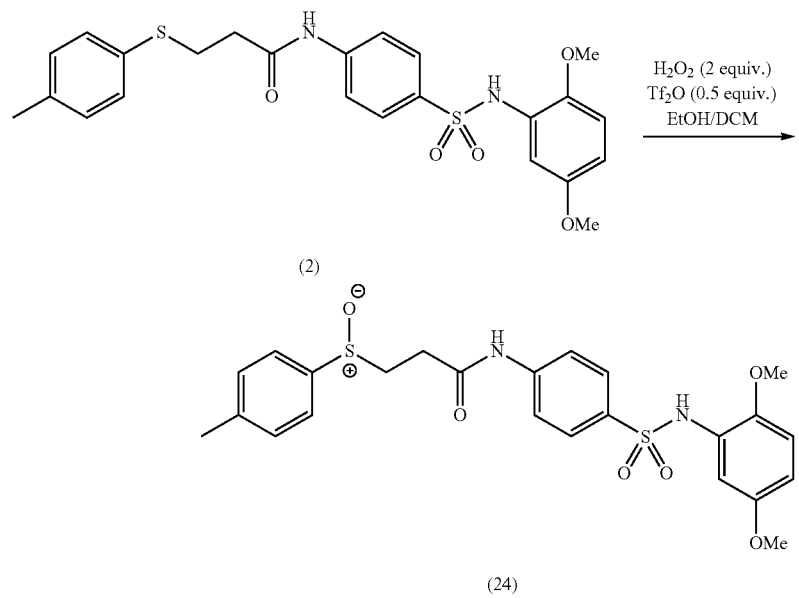

(24)

Scheme 6

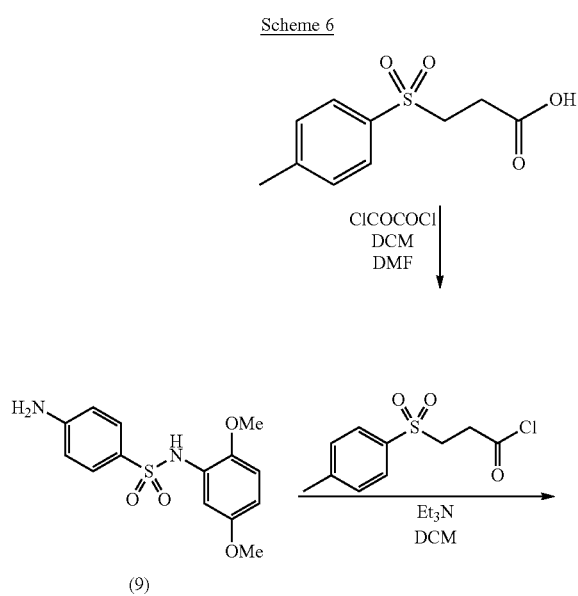

As another representative examples of the embodiment, schemes 7 and 8 present sulfonamides bearing additional functional groups on nitrogen atoms. Functionalization of the free NH of sulfonamide is obtained by alkylation under basic conditions of the nitrobenzene sulfonamide derivatives. After subsequent reduction of the nitro group and acylation of the resulting primary anilines, these chemical transformations give access to N-disubstituted sulfonamides as depicted with the example (26) in scheme 7. Functionalization of the free NH of sulfonamide is also obtained under acylation conditions as depicted in scheme 8.

Scheme 7

Scheme 8

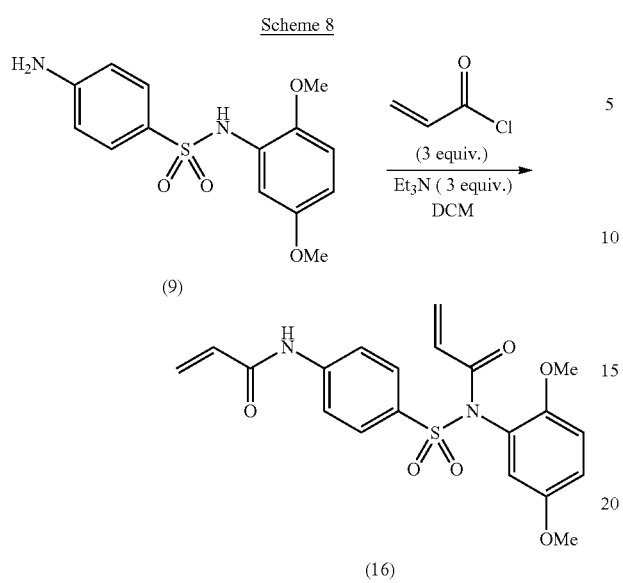

General Experimental Details

Solvents were purified and dried by standard methods prior to use; alternatively, the MB SPS-800-dry solvent system was used to dry dichloromethane. Commercially available reagents were purchased from Sigma Aldrich and were used without purification. Dry dichloromethane was obtained by refluxing solvent on calcium hydride for an hour and distilled under argon. Glassware used for reaction was either flame dried under vacuum or under argon stream for several minutes. Reactions were carried out under rigorous anhydrous conditions and argon stream/positive pressure of argon. $^1$H and $^{13}$C NMR spectra were recorded on a Bruker Avance 300 spectrometer fitted with a 5 mm i.d. BBO probe carefully tuned to the recording frequency of 300.13 MHz (for $^1$H) and 75.47 MHz (for $^{13}$C), the temperature of the probe was set at room temperature (around 293-294 K), on a Bruker Avance 400 spectrometer fitted with a 5 mm i.d. BBFO+ probe carefully tuned to the recording frequency of 400.13 MHz (for $^1$H) and 100.61 MHz (for $^{13}$C). The spectra are referenced to the solvent in which they were run (7.26 ppm for $^1$H CDCl$_3$ and 77.16 ppm for $^{13}$C CDCl$_3$, 2.5 ppm for $^1$H DMSO and 39.52 ppm for $^{13}$C DMSO). Chemical shifts (δ) are given in ppm, and coupling constants (J) are given in Hz with the following splitting abbreviations: s=singlet, d=doublet, t=triplet, q=quartet, qt=quintet, sx=sextuplet, sp=septuplet, m=massif and br=broad. All assignments were confirmed with the aid of two-dimensional $^1$H, $^1$H (COSY), or $^1$H, $^{13}$C (HSQC, HMBC) experiments using standard pulse programs. All reactions were monitored by TLC on commercially available precoated plates (Kieselgel 60 F254), and the compounds were visualized with KMnO$_4$ solution [KMnO$_4$ (3 g), K$_2$CO$_3$ (20 g), NaOH (5% aq.; 5 mL), H$_2$O (300 mL)] and heating or by UV (254 nm) when possible. Flash column chromatography was carried out using high purity grade (Merck grade 9385) pore size 60 Å, 230-400 mesh particle size silica gel (Sigma Aldrich). Solvents used for chromatography were prior distilled on a Buchi rotavapor R-220-SE. Low resolution mass spectrometry (MS) were recorded on a ThermoFinnigan DSQII quadripolar spectrometer (coupled with a Trac-Ultra GC apparatus) for Chemical Ionization (CI), on a ThermoFinnigan LCQ Advantage spectrometer for Electro-Spray Ionisation (ESI). High resolution mass spectrometry (HRMS) were recorded on a ThermoFinnigan MAT95XL spectrometer (for CI) and on a ThermoFisher Scientific LTQ-Orbitrap spectrometer (for ESI).

Example 1:
N-(2,4-dimethoxyphenyl)-4-nitrobenzenesulfonamide

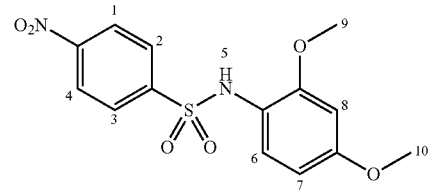

To a solution of 2,4-dimethoxyaniline (4.87 g, 31.59 mmol) dissolved in dried DCM (175 mL) was added pyridine (2.56 mL, 31.59 mmol). The 4-nitrobenzenesulfonyl chloride (7 g, 31.59 mmol), also dissolved in dried DCM, was added dropwise. After 24 hours of stirring at room temperature, the reaction mixture was quenched with water. After extraction with DCM, the organic layers were washed with aqueous solution of 10% K$_2$CO$_3$, followed by aqueous saturated solution of NaCl. After drying with MgSO$_4$, the crude was obtained by filtration and concentration under vacuum. The crude mixture was purified by chromatography over a silica gel column (PE/AcOEt: 7/3) and afforded the expected N-(2,4-dimethoxyphenyl)-4-nitrobenzenesulfonamide (7.8 g, 23 mmol) as a light brown solid with 78% yield. (Rf=0.82 (EP/EtOAc: 1/1)); mp=161° C. RMN $^1$H (300 MHz, CDCl$_3$): 8.22 (d, 2H, H$^1$-H$^4$), 7.84 (d, 2H, H$^2$-H$^3$), 7.46 (d, 1H, H$^8$), 6.66 (s, 1H, H$^5$), 6.47 (dd, 1H, H$^7$), 6.27 (d, 1H, H$^6$), 3.77 (s, 3H, H$^{10}$), 3.47 (s, 3H, H$^9$). RMN $^{13}$C (75 MHz, CDCl$_3$): 159.2 (C$^{IV}$), 152.1 (C$^{IV}$), 150.0 (C$^{IV}$), 144.9 (C$^{IV}$), 128.6 (C$^2$-C$^3$), 125.7 (C$^8$), 123.7 (C$^1$-C$^4$), 117.2 (C$^{IV}$), 104.6 (C$^7$), 98.7 (C$^6$), 55.5 (CH$_3$), 55.4 (CH$_3$). HRMS: Calculated for [M+Na]$^+$ 361.0470; Measured: 361.0470. IR: 3269 (v N—H), 3109 (v Car-H), 2840 (v OC—H), 1523 (v$_{as}$ NO$_2$), 1352 (v$_s$ NO$_2$), 128 (v$_{as}$ SO$_2$), 1159 (v$_s$ SO$_2$).

Example 2:
N-(2,5-dimethoxyphenyl)-4-nitrobenzenesulfonamide
(9)

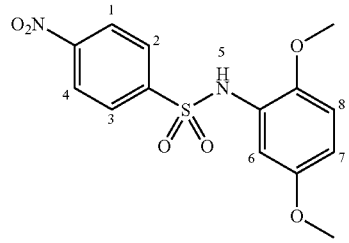 [SMILES: COc1ccc(OC)c(NS(=O)(=O)c2ccc([N+](=O)[O-])cc2)c1]

To a solution of 2,5-dimethoxyaniline (4.87 g, 31.59 mmol) in DCM (175 mL) were subsequently added dropwise pyridine (2.56 mL, 31.59 mmol) and a solution of 4-nitrobenzenesulfonyl chloride (7 g, 31.59 mmol) in DCM. After 24 hours of stirring at room temperature, the reaction mixture was quenched with H$_2$O. After extraction three times with DCM, the organic layer was washed with an aqueous solution of 10% K$_2$CO$_3$, and a saturated aqueous solution of NaCl. After drying with MgSO$_4$, filtration and concentration under vacuum, the crude was purified by chromatography over silica gel (PE/AcOEt: 7/3) and afforded the expected compound (9) as a yellow solid (7.8 g, 23 mmol) with 78% yield. (Rf=0.88 (EP/EtOAc: 1/1)); mp=165° C. RMN $^1$H (300 MHz, CDCl$_3$): 8.24 (d, 2H, H$^1$-H$^4$), 7.94 (d, 2H, H$^2$-H$^3$), 7.17 (d, 1H, H$^6$), 7.06 (s, 1H, H$^5$), 6.67 (dd, 1H, H$^8$), 6.61 (d, 1H, H$^7$), 3.77 (s, 3H, CH$_3$), 3.59 (s, 3H, CH$_3$). RMN $^{13}$C (75 MHz, CDCl$_3$): 159.0 (C$^{IV}$), 150.2 (C$^{IV}$), 144.8 (C$^{IV}$), 143.9 (C$^{IV}$), 128.5 (C$^2$-C$^3$), 125.4 (C$^{IV}$), 124.0 (C$^1$-C$^4$), 111.5 (C$^8$), 110.8 (C$^7$), 108.3 (C$^6$), 56.7 (CH$_3$), 55.8 (CH$_3$). HRMS: Calculated for [M+Na]$^+$ 361.0470; Measured: 361.0470. IR: 3310 (v N—H), 3107 (v Car-H), 2841 (v OC—H), 1534 (v$_{as}$ NO$_2$), 1391 (v$_s$ NO$_2$), 1345 (v$_{as}$ SO$_2$), 1157 (v$_{as}$ NO$_2$)

Example 3:
N-(2-methoxyphenyl)-4-nitrobenzenesulfonamide
(17)

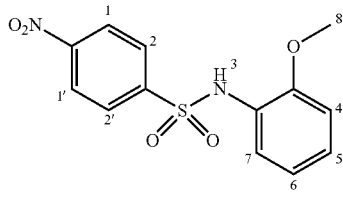 [SMILES: COc1ccccc1NS(=O)(=O)c1ccc([N+](=O)[O-])cc1]

To a solution of o-anisidine (2 mL, 15 mmol) in DCM (40 mL) were subsequently added dropwise dry pyridine (1.15 mL, 15 mmol) and a solution of 4-nitrobenzenesulfonyl chloride (3.32 g, 15 mmol) in DCM (40 mL). After 24 hours of stirring at room temperature, the reaction mixture was quenched with H$_2$O (80 mL). After extraction three times with DCM, the organic layer was washed with an aqueous solution of 10% K$_2$CO$_3$ (60 mL), and a saturated aqueous solution of NaCl (60 mL). After drying with MgSO$_4$, filtration and concentration under vacuum, the crude was purified by chromatography over silica gel (PE/EtOAc: 90/10 to 0/100) affording the expected compound (17) as a yellow solid (4.28 g, 13.9 mmol) with 93% yield. ((Rf=0.74 (PE/EtOAc: 7/3), mp=156.5° C.)$^1$H NMR (300 MHz, CDCl$_3$) δ 8.23 (dt, J$_{2-2'}$=2.1 Hz, J$_{2-1}$=9.0 Hz, 2H, H$_2$ and H$_{2'}$), 7.91 (dt, J$_{1-1'}$=2.1 Hz, J$_{1-2}$=9.0 Hz, 2H, H$_1$ and H$_{1'}$), 7.55 (dd, J$_{7-5}$=1.6 Hz, J$_{7-6}$=7.8 Hz, 1H, H$_7$), 7.10 (dt, J$_{6-4}$=1.6 Hz, J$_{6-7}$=7.8 Hz, 1H, H$_6$), 7.04 (bs, 1H, H$_3$), 6.94 (dt, J$_{6-4}$=1.2 Hz, J$_{5-4}$=7.8 Hz, 1H, H$_5$), 6.74 (dd, J$_{4-5}$=7.8 Hz, 1H, H$_4$), 3.62 (s, 3H, H$_8$) $^{13}$C NMR (75 MHz, CDCl$_3$) δ 150.3, 150.0, 145.0 (C$^{IV}$ Ar) 128.6 (C$_2$ and C$_{2'}$), 126.7 (C$_6$), 124.0 (C$_1$ and C$_{1'}$), 122.3 (C$_7$), 121.4 (C$_5$), 110.9 (C$_4$), 77.4 (C$^{IV}$ Ar) 55.7 (C8) MS (EI, m/z): [M$^+$.]=308.0 HRMS: Calculated for [M+Na]$^+$ 331.0356; Measured: 331.0359. IR (cm$^{-1}$): 3244 (vNH), 3100 (v=C—H), 1525 (v NO$_2$), 1310 (v$_{as}$ SO$_2$).

Example 4:
N-(3-methoxyphenyl)-4-nitrobenzenesulfonamide
(21)

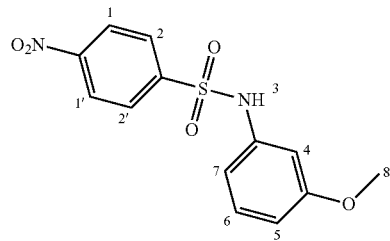 [SMILES: COc1cccc(NS(=O)(=O)c2ccc([N+](=O)[O-])cc2)c1]

To a solution of m-anisidine (2 ml, 15 mmol) in DCM (40 mL) were subsequently added dropwise dry pyridine (1.15 mL, 15 mmol) and a solution of 4-nitrobenzenesulfonyl chloride (4.54 g, 14.6 mmol) in DCM (40 mL). After 24 hours of stirring at room temperature, the reaction mixture was quenched with H$_2$O (80 mL). After extraction three times with DCM, the organic layer was washed with an aqueous solution of 10% K$_2$CO$_3$ (60 mL), and a saturated aqueous solution of NaCl (60 mL). After drying with MgSO$_4$, filtration and concentration under vacuum, the crude was purified by chromatography over silica gel (PE/EtOAc: 90/10 to 0/100) affording the expected compound (21) as a yellow solid (4.53 g, 14.7 mmol) with 98% yield. (Rf=0.58 (PE/EtOAc: 5/5); mp=119.4° C.). $^1$H NMR (300 MHz, CDCl$_3$): δ 8.27 (dt, J$_{2-2'}$=2.1 Hz, J$_{2-1}$=9.0 Hz, 2H, H$_2$ and H$_{2'}$), 7.97 (dt, J$_{1-1'}$=2.1 Hz, J$_{1-2}$=9.0 Hz, 2H, H$_1$ and H$_{1'}$), 7.15 (m, 1H, H$_7$), 7.09 (s, 1H, H$_3$), 6.69 (m, 2H, H$_4$ and H$_6$), 6.62 (m, 1H, H$_5$), 3.75 (s, 3H, H$_8$) $^{13}$C NMR (75 MHz, CDCl$_3$) δ 160.6, 150.4, 144.6, 136.7 (C$^{IV}$ Ar) 130.6 (C$_7$), 128.7 (C$_1$ and C$_{1'}$), 124.4 (C$_2$ and C$_{2'}$), 114.0 (C$_5$), 121.5 (C$_5$), 111.7, 108.1 (C$_4$ and C$_6$), 55.5 (C$_8$) MS (EI, m/z): [M$^+$.]=308.0 HRMS: Calculated for [M+H]$^+$ 309.0537; Measured: 309.0540. IR (cm$^{-1}$): 3245 (vNH), 3113 (v=C—H), 1528 (v NO$_2$), 1306 (v$_{as}$ SO$_2$)

Example 5:
N-(2,4-dimethoxyphenyl)-4-nitrobenzenesulfonamide

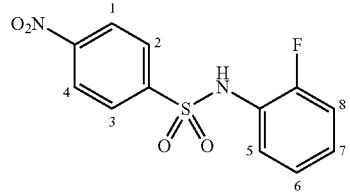

To a solution of 4-fluoroaniline (15 mmol, 1.45 mL) dissolved in dry DCM (60 mL) were added dropwise pyridine (15 mmol, 1.15 mL) and the 4-nitrobenzene-1-sulfonyl chloride (15 mmol, 3.32 g) dissolved in dry DCM. After stirring at room temperature over 24 hours, the reaction mixture was quenched with water. The aqueous layer was extracted twice with DCM. The combined organic layers were washed with H$_2$O, then an aqueous solution of 10% K$_2$CO$_3$, and an aqueous saturated solution of NaCl. After drying with MgSO$_4$, filtration and concentration under vacuum, the crude was purified by chromatography over silica gel (pure DCM) affording N-(2,4-dimethoxyphenyl)-4-nitrobenzenesulfonamide (3.3 g; 11.15 mmol) with 75% yield (Rf=0.53 (DCM 100%); mp=166° C.). RMN $^1$H (300 MHz, CDCl$_3$): 8.29 (d, 2H, H$^1$-H$^4$), 7.94 (d, 2H, H$^2$-H$^3$), 7.55-7.65 (m, 1H, H$^6$), 7.10-7.17 (m, 2H, H$^5$-H$^7$), 6.92-7.15 (m, 1H, H$^8$), 6.80 (s, 1H, NH). RMN $^{13}$C (75 MHz, CDCl$_3$): [153.0-156.3] (C—F), 150.6 (C$^{IV}$), 144.6 (C$^{IV}$), 128.6 (C$^2$-C$^3$), [127.7-127.8] (Car), [125.2-125.3] (Car), 124.8 (C$^6$), 124.5 (C$^1$-C$^4$), [123.4-123.6] (C$^{IV}$), [115.8-116.0] (C$^8$). HRMS: Calculated for [M+Na]+ 319.0173; Measured: 319.0165. IR (cm$^{-1}$): 3259 (vNH), 1604, 1519 (v NO$_2$), 1341 (v$_{as}$ SO$_2$); 1309; 1160.

Example 6:
4-amino-N-(2,4-dimethoxyphenyl)benzenesulfonamide

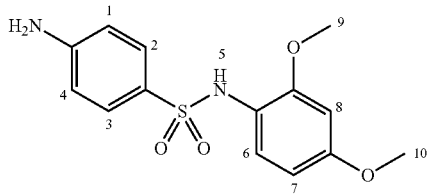

To a solution of N-(2,4-dimethoxyphenyl)-4-nitrobenzenesulfonamide (2 g, 6.48 mmol) in MeOH were successively added iron (1.06 g, 19 mmol) and an aqueous solution of NH$_4$Cl (1.72 g, 32.46 mmol in 20 mL of H$_2$O). After stirring over 60 hours at 70° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over MgSO$_4$ and the solvents were concentrated under vacuum. The crude was purified by chromatography over silica gel (PE/EtOAc: 1/1) affording the expected compound as a light brown solid (1.37 g, 4.44 mmol) with 68% yield. (Rf: 0.22 (EP/EtOAc: 1/1); mp: 115° C.). RMN $^1$H (300 MHz, CDCl$_3$): 7.41 (d, 2H, H$^2$-H$^3$), 7.37 (d, 1H, H$^8$), 6.562 (s, 1H, H$^5$), 6.537 (d, 2H, H$^1$-H$^2$), 6.420 (dd, 1H, H$^8$), 6.280 (d, 1H, H$^6$), 3.754 (s, 3H, H$^{10}$), 3.534 (s, 3H, H$^9$). RMN $^{13}$C (75 MHz, CDCl$_3$): 158.153 (C$^6$), 151.798 (C$^5$), 150.448 (C$^0$), 129.404 (C3-C4), 127.423 (C$^4$'), 124.273 (C$^7$), 119.209 (C$^5$), 113.601 (C$^1$-C$^2$), 104.216 (C$^8$), 98.756 (C$^6$), 55.533 (C$^{10}$), 55.487 (C$^9$) HRMS: Calculated for [M+Na]$^+$ 331.0728; Measured: 331.0723. IR: 3362 (v$_{as}$ NH$_2$), 2937 (v Car-H), 2837 (v OC—H), 1590 (δ NH$_2$), 1207 (v Csp$^2$-O-Csp$^3$)

Example 7:
4-amino-N-(2,5-dimethoxyphenyl)benzenesulfonamide (10)

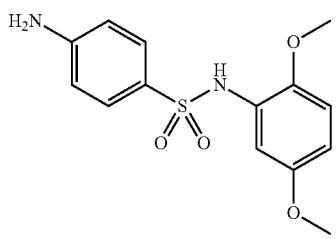 [SMILES: COc1ccc(OC)c(NS(=O)(=O)c2ccc(N)cc2)c1]

To a solution of N-(2,5-dimethoxyphenyl)-4-nitrobenzenesulfonamide (2 g, 6.48 mmol) in MeOH were successively added iron (1.06 g, 19 mmol) and an aqueous solution of NH$_4$Cl (1.72 g, 32.46 mmol in 20 mL of H$_2$O). After stirring over 60 hours at 70° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over MgSO$_4$ and the solvents were concentrated under vacuum. The crude was purified by chromatography over silica gel (PE/EtOAc: 1/1) affording the expected compound (10) as a light brown solid (1.4 g, 4.54 mmol) with 70% yield. (Rf: 0.36 (EP/EtOAc: 1/1); mp: 126° C.). RMN $^1$H (300 MHz, CDCl$_3$): 7.55 (d, 2H, H$^2$-H$^3$), 7.10 (d, 1H, H$^6$), 6.99 (s, 1H, H$^5$), 7.65 (d, 2H, H$^8$), 6.56 (d, 1H, H$^2$-H$^4$), 6.51 (m, 1H, H$^6$), 3.73 (s, 3H, CH$_3$), 3.63 (s, 3H, CH$_3$). RMN $^{13}$C (75 MHz, CDCl$_3$): 154.1 (CO), 151.0 (CO), 143.6 (C$^{IV}$), 130.0 (C$^2$-C$^3$), 127.5 (C$^{IV}$), 127.4 (C$^{IV}$), 112.0 (C$^1$-C$^4$), 111.7 (C$^8$), 109.5 (C$^7$), 106.9 (C$^6$), 56.5 (CH$_3$), 55.9 (CH$_3$). HRMS: Calculated for [M+Na]$^+$ 331.0728; Measured: 331.0728. IR: 3368 (v$_{as}$ NH$_2$), 3008 (v Car-H), 2834 (v OC—H), 1590 (b NH$_2$), 1214 (v Csp$^2$-O-Csp$^3$).

Example 8:
4-amino-N-(2-methoxyphenyl)-benzenesulfonamide (18)

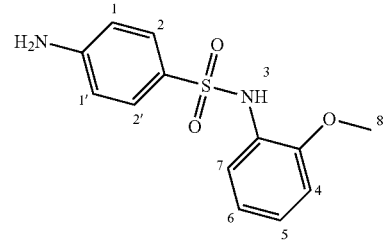 [SMILES: COc1ccccc1NS(=O)(=O)c1ccc(N)cc1]

To a solution of N-(2-methoxyphenyl)-4-nitrobenzenesulfonamide (0.800 g, 2.60 mmol) in MeOH were successively added iron (0.850 g, 15.2 mmol) and an aqueous solution of NH$_4$Cl (1.380 g, 26 mmol in 20 mL of H$_2$O). After stirring over 24 hours at 65° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over MgSO$_4$ and the solvents were concentrated under vacuum. The crude was purified by chromatography over silica gel (80/20 to 0/100) affording the expected compound (18) as a light brown solid (0.61 g, 2.2 mmol) with 84% yield. (Rf=0.26 (PE/EtOAc: 6/4); mp=193.9° C.). $^1$H NMR (300 MHz, DMSO) δ: 8.80 (s, 1H, NH), 7.35 (dd, J$_{7-5}$=1.6 Hz, J$_{7-6}$=7.8 Hz, 1H, H$_7$), 7.03 (m, 1H, H$_6$), 6.90 (dd, J$_{4-6}$=1.3 Hz, J$_{4-5}$=8.1 Hz, 1H, H$_4$), 6.82 (dt, J$_{5-6}$=1.3 Hz, J$_{5-4}$=8.1 Hz, 1H, H$_5$), 6.51 (m, 2H, H$_1$ and H$_{1'}$), 5.92 (s, 2H, NH$_2$) 3.59 (s, 3H, H$_8$) $^{13}$C NMR (75 MHz, DMSO) δ: 152.7, 151.3 (C$^{IV}$Ar), 128.7 (C$_2$), 126.4 (C$^{IV}$Ar), 125.4 (C$_6$), 125.2 (C$^{IV}$Ar), 122.9 (C$_7$), 120.3 (C$_4$), 112.2 (C$_1$), 111.6 (C$_5$), 55.5 (C$_8$) MS (EI, m/z): [M$^+$.]=278.0 HRMS: Calculated for [M+H]$^+$ 279.0798; Measured: 279.0796. IR (cm$^{-1}$): 3458 (v NH$_{ar}$), 3366 (v$_s$ NH$_{2ar}$), 3328 (v$_{as}$ NH$_{2ar}$), 1315 (v$_{as}$ SO$_2$)

Example 9: 4-amino-N-(2-methoxyphenyl)-benzenesulfonamide (25)

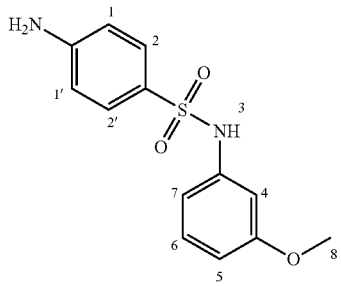

To a solution of 4-amino-N-(2-methoxyphenyl)-benzenesulfonamide (1.2 g, 3.9 mmol) in MeOH were successively added iron (1.28 g, 22.8 mmol) and an aqueous solution of $NH_4Cl$ (2.07 g, 39 mmol in 30 mL of $H_2O$). After stirring over 6 hours at 65° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over $MgSO_4$ and the solvents were concentrated under vacuum. The crude was purified by chromatography over silica gel (80/20 to 0/100) affording the expected compound A427 as a light brown solid (0.73 g, 2.6 mmol) with 67% yield. (Rf=0.26 (PE/EtOAc: 6/4); mp=140.6° C.). $^1$H NMR (300 MHz, $CDCl_3$) δ 7.54 (m, 2H, $H_2$ and $H_{2'}$), 7.49 (m, 1H, $H_7$), 7.00 (m, 1H, $H_6$), 6.95 (bs, 1H, $H_3$), 6.87 (dt, $J_{6-4}$=1.2 Hz, $J_{5-4}$=7.8 Hz, 1H, $H_5$), 6.74 (dd, $J_{4-6}$=1.2 Hz, $J_{4-5}$=7.8 Hz, 1H, $H_4$), 6.56 (m, 2H, $H_1$ and $H_{1'}$), 3.67 (s, 3H, $H_8$) $^{13}$C NMR (100 MHz, $CDCl_3$) δ: 160.5, 150.9, 138.3 ($C^{IV}$Ar), 130.1 ($C_2$), 129.6 ($C_2$), 114.1 ($C_{ar}$), 113.7 ($C^{Iv}$Ar), 113.5 ($C_{ar}$), 110.9 ($C_{ar}$), 107.1 ($C_5$), 55.5 ($C_8$) MS (EI, m/z): [M$^+$.]=278.1 HRMS: Calculated for [M+H]$^+$ 279.0798; Measured: 279.0796. IR (cm$^{-1}$): 3407 (v $NH_{ar}$), 3338 ($v_s$ $NH_{2ar}$), 3139 (v=C—H), 1315 ($v_{as}$ $SO_2$)

Example 10: N-(2,4-dimethoxyphenyl)-4-aminobenzenesulfonamide

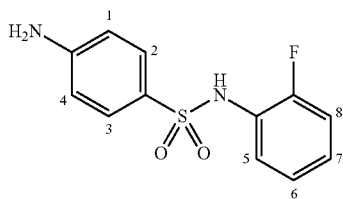

N-(2,4-dimethoxyphenyl)-4-nitrobenzenesulfonamide (11.15 mmol, 3.30 g) was dissolved in methanol (125 mL). Ammonium chloride (113 mmol, 6 g), dissolved in distillated water (67 mL), and iron (65.33 mmol, 3.65 g) were then added to the reaction mixture. After stirring overnight at 65° C., the reaction mixture was filtered through a pad of celite on sintered funnel. After successive washings with acetone, DCM and ethyl acetate, the biphasic mixture was separated. The aqueous layer was extracted twice with DCM. The combined organic layers were dried over $MgSO_4$ and the solvents were concentrated under vacuum. The crude was purified by chromatography over silica gel affording N-(2,4-dimethoxyphenyl)-4-nitrobenzenesulfonamide (7.89 mmol, 2.10 g) with 70% yield. (Rf: 0.44 (DCM 100%); mp=190° C.). RMN $^1$H (300 MHz, DMSO-d6): 8.41 (s, 1H, NH), 7.34 (d, 2H, $H^2$-$H^3$), 7.21-7.25 (m, 1H, $H^6$), 7.09-7.12 (m, 3H, $H^5$-$H^7$-$H^8$), 6.54 (d, 2H, $H^1$-$H^4$), 5.96 (s, 2H, $NH_2$). RMN $^{13}$C (75 MHz, DMSO-d6): [154.0-156.4] (C—F), 152.9 ($C^{IV}$), 128.6 ($C^2$-$C^3$), [126.3-126.4] (Car), 125.6 ($C^6$), [125.2-125.3] ($C^{IV}$), 124.7 ($C^{IV}$), [124.3-124.4] ($C^{IV}$), [115.7-115.9] ($C^8$), 112.5 ($C^1$-$C^4$). HRMS: Calculated for [M+Na]$^+$ 289.0423; Measured: 289.0435 IR (cm$^{-1}$): 3402 (v $NH_{ar}$), 3337 ($v_s$ $NH_{2ar}$), 1644, 1592, 1495, 1318 ($v_{as}$ $SO_2$), 1148, 1090.

Example 11: N-(4-(N-(2,4-dimethoxyphenyl)sulfamoyl)phenyl)-3-(p-tolylthio)propanamide (1)

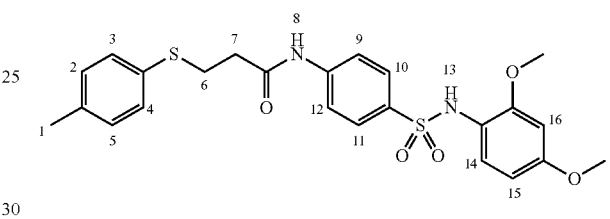

In a 50 mL flask, 3-(p-tolylthio)propanoic acid (0.5 g, 2.55 mmol) was dissolved in dry DCM (10 mL) under argon atmosphere. Oxalyl chloride (0.22 mL, 2.55 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio)propanoyl chloride in dry DCM (15 mL) were added dropwise at 0° C. 4-amino-N-(2,4-dimethoxyphenyl)benzenesulfonamide (0.7 g, 2.55 mmol) dissolved in 2 mL of dry DCM and few crystals of DMAP. After stirring at room temperature over 48 hours, the reaction mixture was quenched with 5% sodium bicarbonate solution. The aqueous layer was extracted three times with DCM. The combined organic layers were washed successively with a molar solution of HCl, and then with brine. After drying over $MgSO_4$ and removal under vacuum of the solvent, the crude was purified by chromatography over silica gel (PE/EtOAc 7/3 to 6/4) affording the expected compound (1) as a white solid (480 mg, 0.99 mmol) with 40% yield. (Rf: 0.46 (EP/EtOAc: 1/1); mp: 153° C.). RMN $^1$H (300 MHz, $CDCl_3$): 7.59 (d, 2H, $H^{10}$-$H^{11}$), 7.49 (d, 2H, $H^9$-$H^{12}$), 7.41 (d, 1H, $H^{14}$), 7.27 (d, 2H, $H^3$-$H^4$), 7.10 (d, 2H, $H^2$-$H^5$), 6.63 (s, 1H, $H^{13}$), 6.42 (dd, 1H, $H^{15}$), 6.26 (d, 1H, $H^{16}$), 3.75 (s, 3H, $CH_3$), 3.49 (s, 3H, $CH_3$), 3.21 (t, 2H, $H^6$), 2.63 (t, 2H, $H^7$), 2.31 (s, 3H, $H^1$). RMN $^{13}$C (75 MHz, $CDCl_3$): 169.76 (CO), 158.6 (CO), 152.0 (CO), 141.7 ($C^{IV}$), 137.3 ($C^{IV}$), 134.1 ($C^{IV}$), 131.0 ($C^{IV}$), 130.9 ($C_3$-$C_4$), 130.1 ($C_2$-$C_5$), 128.7 ($C_{10}$-$C_{11}$), 124.7 ($C^{14}$), 119.0 ($C_9$-$C_{12}$), 118.6 ($C^{IV}$), 104.5 ($C^{15}$), 98.9 ($C^{16}$), 55.7 ($CH_3$), 55.6 ($CH_3$), 37.3 ($C^7$), 30.0 ($C^6$), 21.2 ($C^1$). HRMS: Calculated for [M+Na]$^+$ 509.1180; Measured: 509.1175. IR: 3358 (v N—H), 3263 (v N—H), 3001 (v Car-H), 2936 (v Cal-H), 2837 (v OC—H), 1687 (v C=O), 1326 ($v_{as}$ $SO_2$), 1303 (Amide III), 1160 ($v_s$ $SO_2$).

Example 12: N-(4-(N-(2,5-dimethoxyphenyl)sulfamoyl)phenyl)-3-(p-tolylthio)propanamide (2)

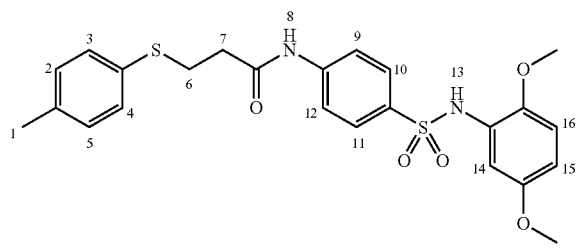

In a 50 mL flask, 3-(p-tolylthio)propanoic acid (0.38 g, 1.95 mmol) was dissolved in dry DCM (10 mL) under argon atmosphere. Oxalyl chloride (0.17 mL, 1.95 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio)propanoyl chloride in dry DCM (10 mL) were added dropwise at 0° C. 4-amino-N-(2,5-dimethoxyphenyl)benzenesulfonamide (0.6 g, 1.95 mmol) and Et$_3$N (0.15 mL, 1.95 mmol) dissolved in dry DCM (10 mL). After stirring at room temperature over 48 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (EP/AcOEt/DCM: 5/2/3, then EP/AcOEt: 1/1) affording the expected compound (2) as a white solid (0.745 g, 1.53 mmol) with 78% yield. (Rf: 0.56 (EP/EtOAc: 1/1); mp: 136° C.). RMN $^1$H (300 MHz, CDCl$_3$): 7.72 (d, 2H, H$^{10}$-H$^{11}$), 7.53 (m, 2H, H$^9$-H$^{12}$-H$^{13}$), 7.29 (d, 2H, H$^9$-H$^{12}$), 7.12 (m, 4H, H$^2$-H$^5$-H$^{14}$), 6.65 (d, 1H, H$^{16}$), 6.52 (dd, 1H, H$^{15}$), 3.74 (s, 3H, CH$_3$), 3.62 (s, 3H, CH$_3$), 3.21 (t, 2H, H$^6$), 2.62 (t, 2H, H$^7$), 2.31 (s, 3H, H$^1$). RMN $^{13}$C (75 MHz, CDCl$_3$): 169.6 (CO), 153.9 (CO), 143.5 (CO), 141.8 (C$^{IV}$), 137.2 (C$^{IV}$), 134.0 (C$^{IV}$), 130.9 (C$_3$-C$_4$), 130.7 (C$^{IV}$), 130.0 (C$_2$-C$_5$), 128.6 (C$^{10}$-C$^{11}$), 126.5 (C$^{IV}$), 119.0 (C$^9$-C$^{12}$), 111.5 (C$^{16}$), 109.7 (C$^{15}$), 107.0 (C$^{14}$), 56.2 (CH$_3$), 55.8 (CH$_3$), 37.2 (C$^7$), 29.9 (C$^8$), 21.0 (C$^1$). HRMS: Calculated for [M+Na]$^+$: 509.1181; Measured: 509.1181. IR: 3308 (v N—H), 3066 (v Car-H), 2952 (v Cal-H), 2832 (v OC—H), 1689 (v C=O), 1329 (v$_{as}$ SO$_2$), 1307 (Amide III), 1148 (v$_s$ SO$_2$)

Example 13: N-(4-(N-(2-methoxyphenyl)sulfamoyl)phenyl)-3-(p-tolylthio) Propanamide (19)

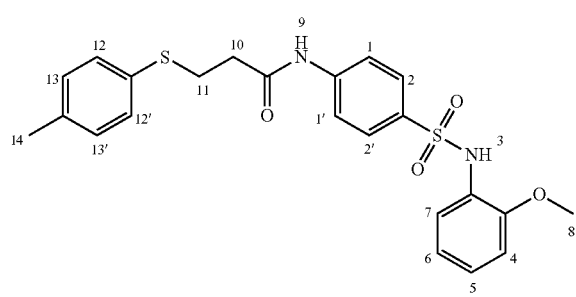

In a 50 mL flask, 3-(p-tolylthio)propanoic acid (1.68 g, 8.40 mmol) was dissolved in dry DCM (25 mL) under argon atmosphere. Oxalyl chloride (1.8 mL, 8.62 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio)propanoyl chloride in dry DCM (10 mL) were added dropwise at 0° C. 4-amino-N-(2-methoxyphenyl)-benzenesulfonamide (0.56 g, 1.81 mmol) and Et$_3$N (0.60 mL, 8.2 mmol) dissolved in dry DCM (20 mL). After stirring at room temperature over 48 hours. After addition of n-Butylamine (1 mL), the reaction mixture was stirred at room temperature over 48 hours. The solvents were removed under vacuum and the crude was purified by recrystallization with EtOAc and PE affording the expected compound (19) as a white solid (0.261 g, 0.5 mmol) with 20% yield. (Rf=0.26 (PE/EtOAc: 7/3); mp=143.5° C.). $^1$H NMR (300 MHz, CDCl$_3$) δ 7.68 (m, 2H, H$_2$ and H$_{2'}$), 7.55 (s, 1H, N—H$_3$ or N—H$_9$), 7.50 (m, 3H, H$_1$, H$_{1'}$, and H$_7$), 7.27 (m, 2H, H$_{12}$ and H$_{12'}$), 7.10 (m, 2H, H$_{13}$ and H$_{13'}$), 7.02 (dt, J$_{7-5}$=1.6 Hz, J$_{7-6}$=7.8 Hz, 1H, H$_6$), 6.98 (s, 1H, N—H$_3$ or N—H$_9$), 6.88 (dt, J$_{6-4}$=1.2 Hz, J$_{5-4}$=7.8 Hz, 1H, H$_5$), 6.73 (dd, J$_{4-6}$=1.2 Hz, J$_{4-5}$=7.8 Hz, 1H, H$_4$), 3.64 (s, 3H, H$_8$), 3.21 (t, J$_{11-10}$=6.9 Hz, 2H, H$_{11}$), 2.61 (t, J$_{10-11}$=6.9 Hz, 2H, H$_{10}$), 2.30 (s, 3H, H$_{14}$) $^{13}$C NMR (75 MHz, CDCl$_3$) δ 169.7, 149.7, 141.9, 137.4, 134.3 (C$^{IV}$ Ar), 131.0 (C$_{12}$), 131.0 (C$^{IV}$ Ar), 130.1 (C$_{13}$), 128.7 (C$_2$), 126.0 (C$_6$), 121.3 (C$_7$), 121.3 (C$_5$), 119.2 (C$_1$), 110.8 (C$_4$), 55.8 (C$_8$), 37.4 (C$_{10}$), 30.1 (C$_{11}$), 21.2 (C$_{14}$) MS (EI, m/z): [M$^+$.]=456.1 HRMS: Calculated for [M+H]$^+$: 457.1250; Measured: 457.1250. IR (cm$^{-1}$): 3359 (v NH$_{ar}$), 3169 (v=C—H), 1692 (v C=O), 1337 (v$_{as}$ SO$_2$), 651 (v C—S).

Example 14: N-(4-(N-(3-methoxyphenyl)sulfamoyl)phenyl)-3-(p-tolylthio) Propanamide (23)

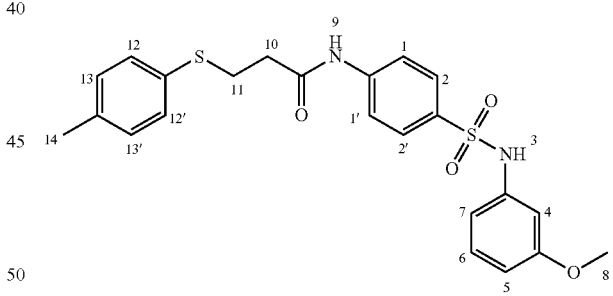

In a 50 mL flask, 3-(p-tolylthio)propanoic acid (0.84 g, 4.31 mmol) was dissolved in dry DCM (20 mL) under argon atmosphere. Oxalyl chloride (0.89 mL, 4.64 mmol) and DMF (0.03 mL) were successively added to the reaction mixture at 0° C. After 15 minutes of stirring, the apparition of bubbles stopped. Oxalyl chloride and DCM were evaporated under vacuum. To a solution of this resulting 3-(p-tolylthio)propanoyl chloride in dry DCM (20 mL) were added dropwise at 0° C. 4-amino-N-(2-methoxyphenyl)-benzenesulfonamide (0.6 g, 2.16 mmol) and Et$_3$N (0.60 mL, 8.2 mmol) dissolved in dry DCM (20 mL). After stirring at room temperature over 48 hours, the solvents were removed under vacuum and the crude was purified by chromatography over silica gel (EP/AcOEt: 1/1), and then recrystallization with EtOAc and PE affording the expected compound

(23) as a white solid (0.168 g, 0.37 mmol) with 17% yield. (Rf=0.26 (PE/EtOAc: 7/3); mp=156.8° C.). $^1$H NMR (300 MHz, CDCl$_3$) δ 7.70 (m, 2H, H$_2$ and H$_{2'}$), 7.59 (s, 1H, N—H$_3$ or N—H$_9$), 7.55 (m, 2H, H$_1$ and H$_{1'}$), 7.28 (m, 2H, H$_{12}$ and H$_{12'}$), 7.11 (m, 3H, H$_{ar}$), 6.62 (m, 4H, H$_{ar}$), 3.74 (s, 3H, H$_8$), 3.22 (t, J$_{11-10}$=6.9 Hz, 2H, H$_{11}$), 2.63 (t, J$_{10-11}$=6.9 Hz, 2H, H$_{10}$), 2.31 (s, 3H, H$_{14}$) $^{13}$C NMR (75 MHz, CDCl$_3$) δ 169.8, 160.5, 142.0, 137.7 (C$^{IV}$ Ar), 134.1 (C$_{ar}$) 131.1 (C$_{12}$), 130.8, 130.3 (C$^{IV}$ Ar), 130.2 (C$_{ar}$), 128.8 (C$_2$), 119.4 (C$_1$), 113.7, 111.2, 107.4, 104.8 (Car), 55.5 (C$_8$), 37.4 (C$_{10}$), 30.1 (C$_{11}$), 21.2 (C$_{14}$) MS (EI, m/z): [M$^+$ ]=456.1 HRMS: Calculated for [M+H]$^+$: 457.1250; Measured: 457.1249. IR (cm-1): 3346 (v NH$_{ar}$), 3180 (v=C—H), 1680 (v C=O), 1332 (v$_{as}$ SO$_2$), 833 (v C—S).

Example 15: N-(4-(N-(2-fluorophenyl)sulfamoyl)phenyl)-3-(p-tolylthio) Propanamide (30)

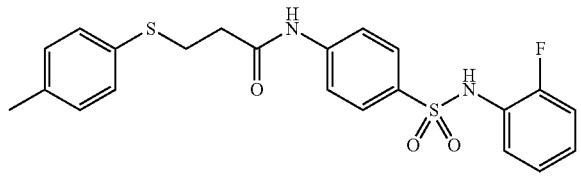 [SMILES: Cc1ccc(SCCC(=O)Nc2ccc(S(=O)(=O)Nc3ccccc3F)cc2)cc1]

In a 25 mL flask, 3-(p-tolylthio)propanoic acid (0.222 g, 1.13 mmol) was dissolved in dry DCM (4 mL) under argon atmosphere. Oxalyl chloride (0.1 mL, 1.13 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (5 mL) were added dropwise at 0° C. 4-amino-N-(2-fluorophenyl)-benzenesulfonamide (0.3 g, 1.13 mmol) and Et$_3$N (0.16 mL, 1.13 mmol) dissolved in dry DCM (5 mL). After stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the expected compound was precipitated off from the crude with cold MeOH crude affording the expected compound (30) as a white solid (Rf: 0.12 (DCM); mp: 162° C.). RMN $^1$H (300 MHz, DMSO-d6): 10.33 (s, 1H, NH), 10.03 (s, 1H, NH), 7.70 (d, 2H, Har), 7.63 (d, 2H, Har), 7.11-7.28 (m, 8H, Har), 3.18 (t, 2H, H6), 2.65 (t, 2H, H7), 2.26 (s, 3H, H1). RMN $^{13}$C (75 MHz, DMSO-d6): 170.0 (CO), [157.3-154.0] (CF), 142.9 (C$^{IV}$), 135.6 (C$^{IV}$), 133.6 (C$^{IV}$), 131.8 (C$^{IV}$), 129.8 (C$^2$-C$^5$), 129.2 (C$^3$-C$^4$), 127.9 (C$^9$-C$^{10}$), [127.3-127.2] (C$^{13}$), 126.5 (C$^{IV}$), [124.7-124.6](C$^{14}$), [124.6-124.4] (C$^{15}$), 118.6 (C$_8$-C$_{11}$), [116.1-115.9] (C$^{12}$), 36.3 (C'), 28.4 (C$^6$), 20.5 (C$^1$). HRMS: Calculated for [M+H]$^+$:445.1056; Measured: 445.1045. IR: 3316 (v N—H), 3019 (v C—H), 1672 (v C=O), 1492 (v C=C), 1332 (v SO$_2$), 653 (δ C—H), 603 (γ N—H).

Example 16: N-(4-(N-(2,5-dimethoxyphenyl)sulfamoyl)phenyl)-4-(p-tolyl) Butanamide (3)

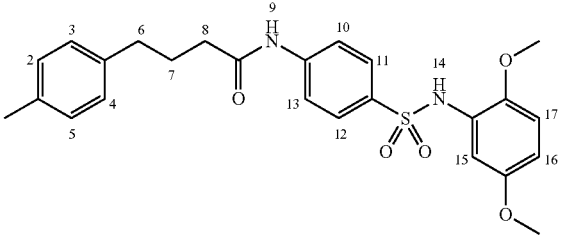

In a 25 mL flask, 3-(p-tolylthio)propanoic acid (0.95 g, 5.43 mmol) was dissolved in dry DCM (17 mL) under argon atmosphere. Oxalyl chloride (0.46 mL, 5.43 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (1.5 mL) were added dropwise at 0° C. 4-amino-N-(2,5-dimethoxyphenyl) benzenesulfonamide (0.56 g, 1.81 mmol) dissolved in 12 mL of dry DCM and Et$_3$N (0.36 mL, 2.7 mmol). After stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (PE/EtOAc: 8/2 to 1/1) affording the expected compound (3) as a white solid (0.250 g, 0.533 mmol) with 30% yield. (Rf: 0.62 (DCM/EtOAc: 9/1); mp: 126° C.). RMN $^1$H (300 MHz, CDCl$_3$): 7.70 (d, 2H, H$^{11}$-H$^{12}$), 7.68 (d, 2H, H$^{10}$-H$^{13}$), 7.45 (s, 1H, H$^{15}$), 7.13 (m, 5H, H$^{2-5}$-H$^{15}$), 6.64 (d, 1H, H$^{17}$), 6.52 (dd, 1H, H$^{16}$), 3.73 (s, 3H, CH$_3$), 3.61 (s, 3H, CH$_3$), 2.63 (t, 2H, H$^8$), 2.32 (m, 5H, H$^1$-H$^6$), 2.01 (q, 2H, H$^7$). RMN $^{13}$C (75 MHz, CDCl$_3$): 171.5 (CO), 153.8 (CO), 143.5 (CO), 142.2 (C$^{IV}$), 138.0 (C$^{IV}$), 135.6 (C$^{IV}$), 133.6 (C$^{IV}$), 129.2-128.6 (C$_{2-5}$), 128.4 (C$_1$-C$_{12}$), 126.5 (C$^{IV}$), 118.9 (C$_{10}$-C$_{13}$), 111.5 (C$^{17}$), 109.7 (C$^{16}$), 107.1 (C$^{15}$), 56.2 (CH$_3$), 55.8 (CH$_3$), 36.7 (C$^7$), 34.5 (C$^8$), 31.0 (C$^6$), 26.7 (C$^7$), 21.0 (C$^1$). HRMS: Calculated for [M+Na]$^+$: 491.1617; Measured: 491.1617 IR: 3316 (v N—H), 3267 (v N—H), 3025 (v Car-H), 2943 (v Cal-H), 2841 (v OC—H), 1663 (v C=O), 1338 (v$_{as}$ SO$_2$), 1312 (Amide III), 1157 (v$_s$ SO$_2$)

Example 17: N-(4-N-(2,5-dimethoxyphenyl)sulfamoyl)phenyl)-2-(p-tolylthio)acetamide (4)

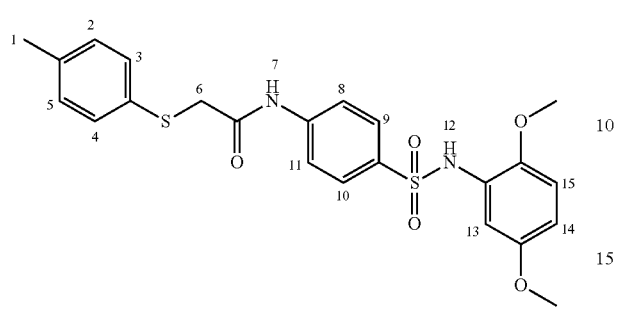

In a 50 mL flask, 3-(p-tolylthio)ethanoic acid (0.99 g, 5.43 mmol) was dissolved in dry DCM (17 mL) under argon atmosphere. Oxalyl chloride (0.46 mL, 5.43 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (1.5 mL) were added dropwise at 0° C. 4-amino-N-(2,5-dimethoxyphenyl)benzenesulfonamide (0.56 g, 1.81 mmol) dissolved in 12 mL of dry DCM and Et$_3$N (0.36 mL, 2.7 mmol). After stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by precipitation in hexane affording the expected compound (4) as a light brown solid (0.55 mg, 1.17 mmol) with 65% yield (Rf: 0.57 (DCM/EtOAc: 9/1); mp: 126° C.). RMN $^1$H (300 MHz, CDCl$_3$): 8.72 (s, 1H, H$^7$), 7.72 (d, 2H, H$^9$-H$^{10}$), 7.54 (d, 2H, H$^8$-H$^{11}$), 7.23 (d, 2H, H$^3$-H$^4$), 7.10 (m, 4H, H$^2$-H$^5$-H$^{12}$-H$^{13}$), 6.64 (d, 1H, H$^{15}$), 6.53 (dd, 1H, H$^{14}$), 3.74 (s, 3H, CH$_3$), 3.71 (s, 2H, H$^6$), 3.60 (s, 3H, CH$_3$). RMN $^{13}$C (75 MHz, CDCl$_3$): 166.8 (CO), 154.0 (CO), 143.6 (CO), 141.5 (C$^{IV}$), 137.9 (C$^{IV}$), 134.5 (C$^{IV}$), 130.5 (C$^3$-C$^4$), 130.0 (C$^{IV}$), 129.4 (C$_2$-C$_5$), 128.7 (C$^9$-C$^{10}$), 126.6 (C$^{IV}$), 119.2 (C$^8$-C$^{11}$), 111.6 (C$^{15}$), 109.8 (C$^{14}$), 107.1 (C$^{13}$), 56.3 (CH$_3$), 55.9 (CH$_3$), 39.4 (C$^6$), 21.2 (C$^1$). HRMS: Calculated for [M+Na]$^+$: 495.1024; Measured: 495.1024. IR: 3354 (ν N—H), 3264 (ν N—H), 3013 (ν Car-H), 2926 (ν Cal-H), 2830 (ν OC—H), 1694 (ν C=O), 1322 (ν$_{as}$ SO$_2$), 1154 (ν$_s$ SO$_2$)

Example 18: N-(4-(N-(2,5-dimethoxyphenyl)sulfamoyl)phenyl)acrylamide (5)

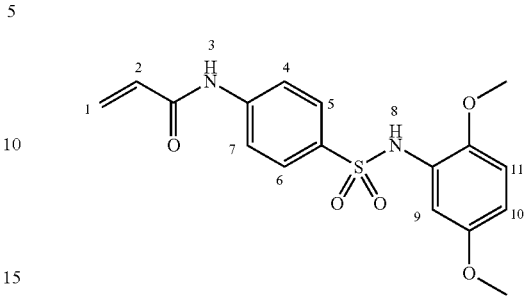

To a solution of 4-amino-N-(2,5-dimethoxyphenyl)benzenesulfonamide (0.3 g, 1.00 mmol) in dry DCM (7.5 mL) were added DIPEA (0.2 mL, 1.17 mmol) and acryloyl chloride (0.10 mL, 1.2 mmol). After stirring overnight, the reaction mixture quenched with an aqueous solution of 5% sodium bicarbonate. The aqueous layer was extracted three times with DCM. The combined organic layers were washed successively with a molar solution of HCl, and then with brine. After drying over Na$_2$SO$_4$ and removal under vacuum of the solvent, the crude was dissolved in dry DCM (2.5 mL). Then, n-butylamine (0.05 mL) was added and the reaction mixture was stirred at room temperature for 12 hours. After addition of hexane, the expected compound A413 was obtained by precipitation as a white solid (0.130 g, 0.36 mmol) with 36% yield. (Rf=0.31 (DCM/EtOAc: 9/1); mp: 126° C.). RMN $^1$H (300 MHz, CDCl$_3$): 7.63 (d, 4H, H$^4$-7), 7.03 (d, 1H, H$^9$), 6.58 (d, 1H, H$^{11}$), 6.48 (dd, 1H, H$^{10}$), 6.35 (d, 1H, H$^1$), 6.25 (dd, 1H, H$^2$), 5.69 (d, 1H, H$^1$), 3.67 (s, 3H, CH$_3$), 3.52 (s, 3H, CH$_3$). RMN $^{13}$C (75 MHz, CDCl$_3$): 164.7 (CO), 153.8 (CO), 144.1 (CO), 142.8 (C$^{IV}$), 133.5 (C$^{IV}$), 130.7 (C$^2$), 128.4 (C$^5$-C$^6$-C$^1$), 126.5 (C$^{IV}$), 119.3 (C$^4$-C$^7$), 111.7 (C$^{11}$), 110.1 (C$^{10}$), 107.8 (C$^9$), 56.2 (CH$_3$), 55.8 (CH$_3$). HRMS: Calculated for [M+Na]$^+$: 385.0834; Measured: 385.0834. IR: 3346 (ν N—H), 3001 (ν Car-H), 2833 (ν OC—H), 1683 (ν C=O), 1332 (ν$_{as}$ SO$_2$), 1284 (δ Amide III), 1156 (ν$_s$ SO$_2$).

Example 19: N-(4-(N-(2,5-dimethoxyphenyl)sulfamoyl)phenyl)-3-(p-tolyloxy)propanamide (6)

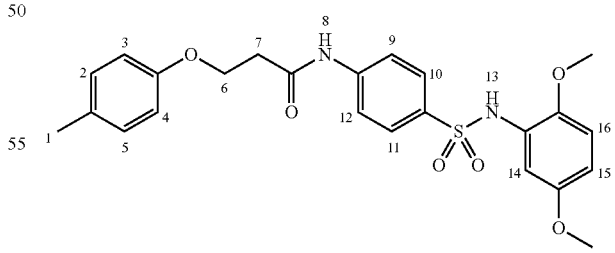

In a 50 mL flask, 3-(p-tolyloxy)propanoic acid (0.36 g, 2 mmol) was dissolved in dry DCM (6.5 mL) under argon atmosphere. Oxalyl chloride (0.17 mL, 2 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolyloxy)propanoyl chloride in dry DCM (4 mL) were added dropwise at 0° C. 4-amino-N-(2,5-dimethoxyphenyl) benzenesulfonamide (0.308 g, 1 mmol) dissolved in 7 mL of dry DCM and Et$_3$N (0.21 mL, 1.5 mmol). After 24 hours of stirring, two equivalents of acyl chloride (0.36 g, 2 mmol) were added. After additional stirring at room temperature over 24 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (PE/EtOAc: 1/1) affording the expected compound (6) as a white solid (0.26 g, 0.55 mmol) with 55% yield (Rf: 0.46 (EP/EtOAc: 1/1); mp: 145° C.). RMN $^1$H (300 MHz, CDCl$_3$): 8.15 (s, 1H, H$^8$), 7.71 (d, 2H, H$^{10}$-H$^{11}$), 7.55 (d, 2H, H$^9$-H$^{12}$), 7.14 (d, 1H, H$^{14}$), 7.10 (d, 2H, H$^3$-H$^4$), 7.03 (s, 1H, H$^{13}$), 6.83 (d, 2H, H$^2$-H$^5$), 6.65 (dd, 1H, H$^{16}$), 6.52 (d, 1H, H$^{15}$), 4.28 (t, 2H, H$^6$), 3.74 (s, 3H, CH$_3$), 3.61 (s, 3H, CH$_3$), 2.82 (t, 2H, H$^7$), 2.31 (s, 3H, H$^1$). RMN $^{13}$C (75 MHz, CDCl$_3$): 169.5 (CO), 155.8 (CO), 154.1 (CO), 143.7 (C$^{IV}$), 142.1 (C$^{IV}$), 134.1 (C$^{IV}$), 131.4 (C$^{IV}$), 130.3 (C$^3$-C$^4$), 128.7 (C$^{10}$-C$^{11}$), 126.7 (C$^{IV}$), 119.3 (C$^9$-C$^{12}$), 114.7 (C$^2$-C$^5$), 111.7 (C$^{16}$), 110.0 (C$^{15}$), 107.3 (C$^{14}$), 64.3 (C$^6$), 56.4 (CH$_3$), 55.9 (CH$_3$), 37.9 (C$^7$), 20.6 (C$^1$). HRMS: Calculated for [M+Na]$^+$: 493.1409; Measured: 493.1410. IR: 3242 (ν N—H), 3065 (ν Car-H), 2837 (ν OC—H), 1677 (ν C═O), 1321 (ν$_{as}$ SO$_2$), 1283 (δ Amide III), 1152 (ν$_s$ SO$_2$)

Example 20: N-(2,5-dimethoxyphenyl)-4-(3-(p-tolylthio)butanamido) Benzamide (8)

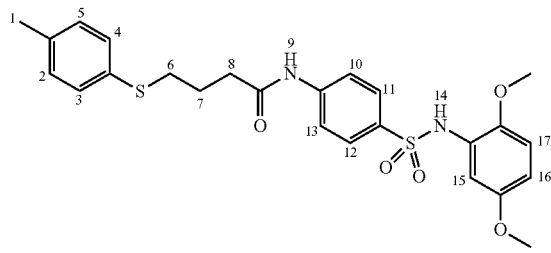

In a 25 mL flask, the 4-(p-tolylthio)butanoic acid (0.42 g, 2 mmol) was dissolved in dry DCM (2 mL) under argon atmosphere. Oxalyl chloride (0.17 mL, 2 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 4-(p-tolylthio)butanoyl chloride in dry DCM (1 mL) were added dropwise at 0° C. 4-amino-N-(2,5-dimethoxyphenyl) benzenesulfonamide (0.2 g, 0.65 mmol) dissolved in 7 mL of dry DCM and Et$_3$N (0.11 mL, 0.78 mmol). After stirring overnight, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by precipitation in iPrOH affording the expected compound (8) as a white solid (0.1 g, 0.35 mmol) with 20% yield. (Rf: 0.12 (DCM); mp: 153° C.). RMN $^1$H (300 MHz, CDCl$_3$): 7.70 (d, 2H, H$^{11}$-H$^{12}$), 7.52 (d, 2H, H$^{10}$-H$^{13}$), 7.40 (s, 1H, H$^9$), 7.24 (d, 2H, H$^3$-H$^4$), 7.13 (d, 1H, H$^{15}$), 7.07 (d, 2H, H$^2$-H$^5$), 7.04 (s, 1H, H$^{14}$), 7.64 (d, 1H, H$^{17}$), 6.53 (dd, 1H, H$^{16}$), 3.74 (s, 3H, CH$_3$), 3.61 (s, 3H, CH$_3$), 2.96 (t, 2H, H$^6$), 2.51 (t, 2H, H$^8$), 2.96 (s, 3H, H$^1$), 2.01 (q, 2H, H$^7$). RMN $^{13}$C (75 MHz, CDCl$_3$): 170.9 (CO), 154.0 (CO), 143.7 (CO), 142.1 (C$^{IV}$), 136.7 (C$^{IV}$), 133.9 (C$^{IV}$), 131.9 (C$^{IV}$), 130.5 (C$^3$-C$^4$), 130.0 (C$^2$-C$^5$), 128.7 (C$^{11}$-C$^{12}$), 126.7 (C$^{IV}$), 119.1 (C$^{10}$-C$^{13}$), 111.6 (C$^{15}$), 109.9 (C$^{17}$), 107.2 (C$^{16}$), 56.4 (CH$_3$), 55.9 (CH$_3$), 35.8 (C$^8$), 33.8 (C$^6$), 24.5 (C$^7$), 21.1 (C$^1$). HRMS: Calculated for [M+Na]$^+$: 523.1337; Measured: 523.1340. IR: 3312 (ν N—H), 3259 (ν N—H), 2917 (ν Car-H), 2832 (ν OC—H), 1666 (ν C═O), 1325 (ν$_{as}$ SO$_2$), 1304 (Amide III), 1157 (ν$_s$ SO$_2$).

Example 21: N-(4-(N-(2,5-dimethoxyphenyl)sulfamoyl)phenyl) Propionamide (11)

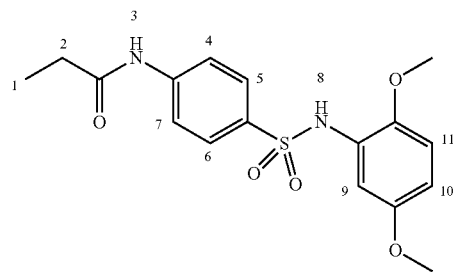 [SMILES: CCC(=O)Nc1ccc(S(=O)(=O)Nc2cc(OC)ccc2OC)cc1]

In a 25 mL flask, the propionic acid (0.36 g, 4.8 mmol) was dissolved in dry DCM (5 mL) under argon atmosphere. Oxalyl chloride (0.41 mL, 4.8 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting propanoyl chloride in dry DCM (2.5 mL) were added dropwise at 0° C. 4-amino-N-(2,5-dimethoxyphenyl)benzenesulfonamide (0.5 g, 1.6 mmol) dissolved in 13 mL of dry DCM and Et$_3$N (0.67 mL, 4.8 mmol). After stirring overnight, the reaction mixture was quenched with 5% sodium bicarbonate solution. The aqueous layer was extracted three times with DCM. The combined organic layers were washed successively with a molar solution of HCl, and then with brine. After drying over Na$_2$SO$_4$ and removal under vacuum of the solvent. Part of the crude (215 mg) was then dissolved in DCM (2 mL) and n-butylamine was added (0.03 mL, 0.26 mmol). The reaction mixture was stirred overnight at room temperature. The expected compound is obtained by precipitation in hexane affording (11) as a white solid (0.150 g, 0.42 mmol) with 73% yield. (Rf: 0.05 (DCM); mp: 170° C.). RMN $^1$H (300 MHz, MeOD): 7.65 (s, 4H, H$^{4-7}$), 7.03 (d, 1H, H$^9$), 6.74 (d, 1H, H$^{11}$), 6.62 (dd, 1H, H$^{10}$), 3.72 (s, 3H, CH$_3$), 3.52 (s, 3H, CH$_3$), 2.39 (q, 2H, H$^2$), 1.18 (t, 3H, H$^1$). RMN $^{13}$C (75 MHz, MeOD): 175.6 (CO), 155.1 (CO), 147.0 (CO), 144.2 (C$^{IV}$), 135.4 (C$^{IV}$), 129.4 (C$^5$-C$^6$), 127.8 (C$^{IV}$), 120.0 (C$^4$-C$^7$), 113.0 (C$^{11}$), 111.6 (C$^{10}$), 111.3 (C$^9$), 56.6 (CH$_3$), 56.1 (CH$_3$), 31.1 (C$^2$), 9.9 (C$^1$). HRMS: Calculated for [M+Na]$^+$: 387.0991; Measured: 387.0977. IR: 3342 (ν N—H), 3171 (ν N—H), 2993 (ν Car-H), 2925 (ν Cal-H), 2834 (ν OC—H), 1689 (ν C═O), 1329 (ν$_{as}$ SO$_2$), 1307 (Amide III), 1152 (ν$_s$ SO$_2$)

Example 22: N-(4-(N-(2,5-dimethoxyphenyl)sulfamoyl)phenyl) Propiolamide (27)

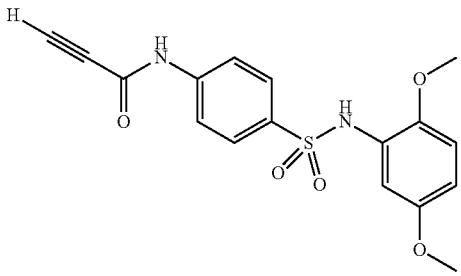 [SMILES: C#CC(=O)Nc1ccc(S(=O)(=O)Nc2cc(OC)ccc2OC)cc1]

To a solution of N-(4-(N-(2,5-dimethoxyphenyl)sulfamoyl)phenyl)-3-(trimethylsilyl)propiolamide (28, 0.460 mmol, 0.200 g) in MeOH (5 mL) was added dropwise 0.7 mL of an aqueous solution of $Na_2B_4O_7 \cdot 10H_2O$ (0.070 mmol, 0.028 g). After stirring over 15 minutes at room temperature, the reaction mixture was quenched with 0.6 mL of HCl (1M). After dilution with water (10 mL), the aqueous layer was extracted three times with DCM. After drying over $Na_2SO_4$ and removal of the solvents under vacuum, the crude was purified by chromatography over silica gel affording the expected compound (27) as a white solid (0.25 mmol, 0.09 g) with 54% yield. (Rf: 0.09 (DCM); mp: 200° C.). RMN $^1$H (300 MHz, DMSO-d6): 11.15 (s, 1H, N$\underline{H}$), 9.42 (s, 1H, N$\underline{H}$), 7.70 (s, 4H, Har), 6.83 (d, 1H, H7), 6.78 (d, 1H, H9), 6.65 (dd, 1H, H8), 4.52 (s, 1H, H1), 3.64 (s, 3H, C$\underline{H}_3$), 3.47 (s, 3H, C$\underline{H}_3$). RMN $^{13}$C (75 MHz, DMSO-d6): 152.8 (s, CO), 150.0 (s, CO), 145.9 (s, CO), 141.7 (s, Car), 135.2 (s, Car), 128.0 (s, Car), 126.3 (s, Car), 119.3 (s, Car), 112.7 (s, C7), 110.4 (s, C9), 110.1 (s, C8), 78.1 (s, C1), 78.0 (s, C2), 56.1 (s, $\underline{C}H_3$), 55.3 (s, $\underline{C}H_3$). HRMS: Calculated for [M+H]$^+$: 361.0858; Measured: 361.0854. IR: 3252 (v N—H), 3230 (v N—H), 2935 (v Car-H), 2837 (v OC—H), 1652 (v C=O), 1312 ($v_{as}$ SO$_2$), 1162 ($v_s$ SO$_2$).

Example 23: N-(4-(N-(2,5-dimethoxyphenyl)sulfamoyl)phenyl)-3-(trimethylsilyl)propiolamide (28)

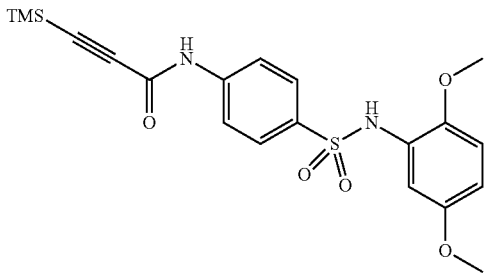 [SMILES: COc1ccc(OC)c(NS(=O)(=O)c2ccc(NC(=O)C#C[Si](C)(C)C)cc2)c1]

In a 10 mL flask, the 3-(trimethylsilyl)propiolic acid (3.24 mmol, 0.460 g) was dissolved in dry DCM (1 mL) under argon atmosphere. Oxalyl chloride (3.24 mmol, 0.27 mL) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(trimethylsilyl)propynoyl chloride in dry DCM (1 mL) were added dropwise at 0° C. 4-amino-N-(2,5-dimethoxyphenyl) benzenesulfonamide (1.62 mmol, 0.500 g) dissolved in 11 mL of dry DCM and Et$_3$N (0.23 mL, 1.62 mmol). After stirring overnight, the reaction mixture was quenched with a saturated solution of NaCl. The aqueous layer was extracted three times with DCM. The combined organic layers were dried over Na$_2$SO$_4$. After removal under vacuum of the solvent, the crude was purified by chromatography over silica gel (DCM/EP: 60/40 to 100/0) affording the expected compound (28) as a white solid (0.45 g, 1.04 mmol) with 64% yield. (Rf: 0.29 (DCM); mp: 84° C.). RMN $^1$H (300 MHz, CDCl$_3$): 7.74 (d, 2H, Har), 7.58 (s, 1H, NH), 7.56 (d, 2H, Har), 7.15 (d, 1H, H7), 7.01 (s, 1H, N$\underline{H}$), 6.65 (d, 1H, H5), 6.56 (dd, 1H, H6), 3.75 (s, 3H, C$\underline{H}_3$), 3.60 (s, 3H, C$\underline{H}_3$), 0.25 (s, 9H, Si—C$\underline{H}_3$). RMN $^{13}$C (75 MHz, CDCl$_3$): 154.0 (s, CO), 150.3 (s, CO), 143.7 (s, CO), 141.3 (s, Car), 134.8 (s, Car), 128.8 (s, Car), 126.5 (s, Car), 119.3 (s, Car), 111.6 (s, C5), 110.1 (s, C6), 107.4 (s, C7), 97.3 (s, Calk), 94.4 (s, Calk), 56.3 (s, $\underline{C}H_3$), 55.9 (s, $\underline{C}H_3$), −0.67 (s, Si—$\underline{C}H_3$). HRMS: Calculated for [M+H]$^+$: 433.1253; Measured: 433.1248. IR: 3232 (v N—H), 2956 (v Car-H), 2835 (v OC—H), 1648 (v C=O), 1313 ($v_{as}$ SO$_2$), 1152 ($v_s$ SO$_2$)

Example 24: Ethyl (4-(N-(2,5-dimethoxyphenyl)sulfamoyl)phenyl) Carbamate (29)

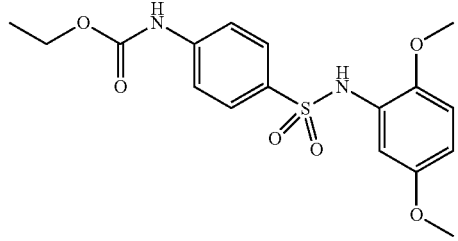 [SMILES: CCOC(=O)Nc1ccc(S(=O)(=O)Nc2cc(OC)ccc2OC)cc1]

To a solution of propiolic acid (0.65 mmol, 0.05 mL) in dry THF under argon atmosphere were added triethylamine (0.65 mmol, 0.08 mL) and then ethyl chloroformate (0.65 mmol, 0.06 mL) at room temperature under argon atmosphere. After 15 minutes of stirring at room temperature, the 4-amino-N-(2,5-dimethoxyphenyl)benzenesulfonamide (0.65 mmol, 0.200 g) was added to the reaction mixture. After stirring over 20 hours, the reaction mixture was quenched by a saturated solution of NaCl. The aqueous layer was extracted three times with DCM. The combined organic layers were dried over Na$_2$SO$_4$. After removal under vacuum of the solvent, the crude was purified by chromatography over silica gel (EP/Et$_2$O: 4/6) affording the non-desired byproduct (29) (0.10 g, 0.25 mmol) as a white solid with 38% yield. Rf: 0.25 (EP/Et$_2$O: 4/6). RMN $^1$H (300 MHz, CDCl$_3$): 7.71 (d, 2H, Har), 7.42 (d, 2H, Har), 7.14 (d, 1H, H7), 7.02 (s, 1H, N$\underline{H}$), 6.79 (s, 1H, N$\underline{H}$), 6.65 (d, 1H, H9), 6.54 (dd, 1H, H8), 4.22 (q, 2H, H2), 3.74 (s, 3H, C$\underline{H}_3$), 3.61 (s, 3H, C$\underline{H}_3$), 1.30 (t, 3H, H1). RMN $^{13}$C (75 MHz, CDCl$_3$): 154.0 (s, CO), 153.1 (s, CO), 143.7 (s, CO), 142.4 (s, Car), 133.1 (s, Car), 128.9 (s, Car), 126.8 (s, Car), 117.8 (s, Car), 111.6 (s, C9), 109.9 (s, C8), 107.2 (s, C7), 61.9 (s, C2), 56.4 ($\underline{C}H_3$), 55.9 ($\underline{C}H_3$), 14.6 (s, C1). HRMS: Calculated for [M+H]$^+$: 381.1120; Measured: 381.1113. IR: 3369 (v N—H), 2996 (v Car-H), 2960 (v Cal-H), 2836 (v OC—H), 1631 (v C=O), 1326 ($v_{as}$ SO$_2$), 1326 ($v_s$ SO$_2$)

Example 25: 2-chloro-N-(4-(N-(2,5-dimethoxyphenyl)sulfamoyl)phenyl) Acetamide (31)

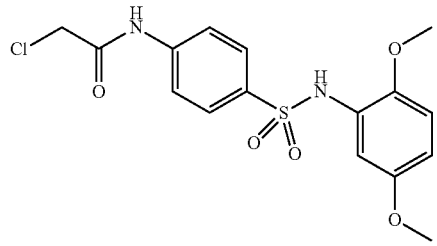 [SMILES: COc1ccc(OC)c(NS(=O)(=O)c2ccc(NC(=O)CCl)cc2)c1]

To a solution of 4-amino-N-(2,5-dimethoxyphenyl)benzenesulfonamide (0.65 mmol, 0.2 g) in DCM (1 mL) were added at 0° C. under argon atmosphere triethylamine (1.1 mmol, 0.15 mL) and 2-chloroacetyl chloride (2 mmol, 0.15 mL). After stirring 24 hours at room temperature, the reaction mixture was quenched with 5% sodium bicarbonate solution. The aqueous layer was extracted three times with DCM. The combined organic layers were washed successively with a molar solution of HCl, and then with brine. After drying over $Na_2SO_4$ and removal under vacuum of the solvent, the crude was purified by chromatography over silica gel (PE/DCM 2/8 to 1/9) affording the expected compound (31) (113 mg, 0.33 mmol) as a white solid with 50% yield. (Rf: 0.25 (DCM/EtOAc: 2/8); mp: 190° C.). RMN $^1$H (300 MHz, DMSO-d6): 10.64 (s, 1H, NH), 9.41 (s, 1H, NH), 7.70 (s, 4H, H$^2$-5), 6.83 (d, 1H, H$^8$), 6.78 (d, 1H, H$^6$), 6.65 (dd, 1H, H$^7$), 4.28 (s, 2H, H$^1$), 3.64 (s, 3H, C$\underline{H}_3$), 3.47 (s, 3H, C$\underline{H}_3$). RMN $^{13}$C (75 MHz, DMSO-d6): 165.3 (s, CO), 152.9 (s, CO), 145.9 (s, CO), 142.1 (s, C$^{IV}$), 134.8 (s, C$^{IV}$), 128.1 (s, C$^3$-C$^4$), 126.3 (s, C$^{IV}$), 118.8 (s, C$^2$-C$^5$), 112.7 (s, C$^8$), 110.5 (s, C$^6$), 110.1 (s, C$^7$), 56.1 (s, $\underline{C}H_3$), 55.3 (s, $\underline{C}H_3$), 43.6 (s, C$^1$). HRMS: Calculated for [M+H]+ 385.0625; Measured: 385.0623. IR: 3254 (v N—H), 1689 (v C=O), 1508; 1330 (v$_{as}$ SO$_2$), 1160.

Example 26: N-(2,5-dimethoxyphenyl)-4-(3-(p-tolylthio)propanamido) Benzamide (7)

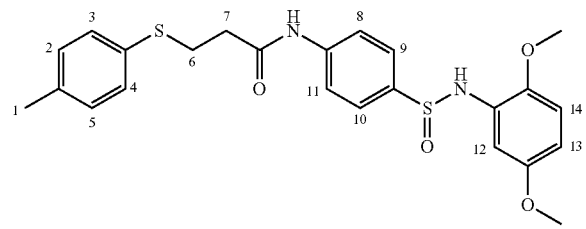

In a 25 mL flask, the 3-(p-tolylthio)propanoic acid (0.588 g, 3 mmol) was dissolved in dry DCM (9 mL) under argon atmosphere. Oxalyl chloride (0.26 mL, 3 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (1 mL) were added dropwise at 0° C. 4-amino-N-(2,5-dimethoxyphenyl)benzamide (0.5 g, 1.6 mmol) dissolved in 7 mL of dry DCM and Et$_3$N (0.17 mL, 1.2 mmol). After stirring over 24 hours, the reaction mixture was quenched with 5% sodium bicarbonate solution. The aqueous layer was extracted three times with DCM. The combined organic layers were washed successively with a molar solution of HCl, and then with brine. After drying over $Na_2SO_4$ and removal under vacuum of the solvent. The crude was purified by chromatography over silica gel (DCM/EtOAc: 100/0 to 9/1) affording the expected compound (7) (0.05 g, 0.11 mmol) as a white solid with 10% yield. (Rf: 0.35 (DCM/EtOAc: 9/1); mp: 153° C.). RMN $^1$H (300 MHz, DMSO-d6): 10.25 (s, 1H, NH), 9.22 (s, 1H, NH), 7.91 (d, 2H, H$^8$-H$^{11}$), 7.71 (d, 2H, H$^9$-H$^{10}$), 7.56 (s, 1H, H$^{12}$), 7.29 (d, 2H, H$^3$-H$^4$), 7.16 (d, 2H, H$^2$-H$^5$), 7.01 (d, 1H, H$^{14}$), 6.72 (dd, 1H, H$^{13}$), 3.80 (s, 3H, CH$_3$), 3.71 (s, 3H, CH$_3$), 3.21 (t, 2H, H$^6$), 2.67 (t, 2H, H$^7$), 2.27 (s, 3H, H$^1$). RMN $^{13}$C (75 MHz, DMSO-d6): 169.7 (CO), 164.2 (CO), 152.9 (CO), 144.9 (CO), 142.2 (C$^{IV}$), 135.6 (C$^{IV}$), 131.9 (C$^{IV}$), 129.8 (C$^2$-C$^5$), 129.1 (C$^3$-C$^4$), 128.6 (C$^{IV}$), 128.4 (C$_8$-C$_{11}$), 127.8 (C$^{IV}$), 118.4 (C$_9$-C$_{10}$), 111.9 (C$^{14}$), 109.7 (C$^{12}$), 109.2 (C$^{13}$). HRMS: Calculated for [M+Na]+: 473.1511; Measured 473.1510. IR: 3316 (v N—H), 3005 (v Car-H), 2912 (v Cal-H), 2838 (v OC—H), 1672 (v C=O), 1366 (v$_{as}$ SO$_2$), 1302 ($\delta$ Amide II), 1163 (v$_s$ SO$_2$)

Example 27: N-(4-(N-(2-methoxyphenyl)sulfamoyl)phenyl)-2-(p-tolylthio) Acetamide (20)

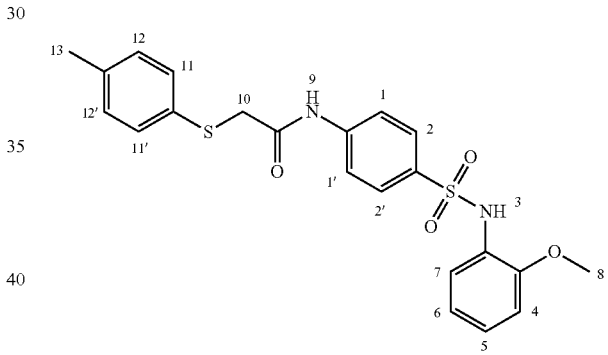

In a 50 mL flask, 3-(p-tolylthio)ethanoic acid (0.38 g, 2.01 mmol) was dissolved in dry DCM (10 mL) under argon atmosphere. Oxalyl chloride (0.4 mL, 2 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl chloride in dry DCM (3 mL) were added dropwise at 0° C. 4-amino-N-(2-methoxyphenyl)benzenesulfonamide (0.286 g, 1 mmol) dissolved in 10 mL of dry DCM and Et$_3$N (0.3 mL, 2 mmol). After stirring at room temperature over 60 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (PE/EtOAc: 7/3 then PE/EtOAc: 4/6) affording the expected compound (20) as a white solid (0.193 g, 1.17 mmol) with 43% yield. (Rf=0.23 (PE/EtOAc: 7/3); mp=169.3° C.). $^1$H NMR (300 MHz, CDCl$_3$) δ 8.70 (s, 1H, N—H$_3$ or N—H$_9$), 7.70 (m, 2H, H$_2$ and H$_{2'}$), 7.52 (m, 3H, $H_1$, $H_{1'}$, and $H_7$), 7.22 (m, 2H, $H_{11}$ and $H_{11'}$), 7.14 (m, 2H, $H_{12}$ and $H_{12'}$), 7.02 (m, 1H, $H_6$), 6.99 (s, 1H, N—$H_3$ or N—$H_9$), 6.88 (dt, $J_{6-4}$=1.2 Hz, $J_{5-4}$=7.8 Hz, 1H, $H_5$), 6.72 (dd, $J_{4-6}$=1.2 Hz, $J_{4-5}$=7.8 Hz, 1H, $H_4$), 3.7 (s, 2H, $H_{10}$), 3.64 (s, 3H, $H_8$), 2.30 (s, 3H, $H_{13}$) $^{13}$C NMR (75 MHz, CDCl$_3$) δ 166.6, 149.3, 141.2, 135.4, 134.7 ($C^{IV\,Ar}$), 130.4 ($C_{12}$), 129.8 ($C^{IV}$ Ar), 129.3 ($C_{13}$), 128.6 ($C_2$), 125.4 ($C_6$) 121.1 ($C_1$), 121.0 ($C_5$), 119.0 ($C_7$), 110.6 ($C_4$), 55.8 ($C_8$), 37.4 ($C_{10}$), 30.1 ($C_{11}$), 21.2 ($C_{14}$) MS (EI, m/z): [M$^+$.]=442.1 HRMS: Calculated for [M+H]$^+$: 443.1094; Measured 443.1093. IR (cm$^{-1}$): 3223 (v NH$_{ar}$), 3113 (v=C—H), 1679 (v C=O), 1339 ($v_{as}$ SO$_2$), 690 (v C—S).

Example 28: N-(4-(N-(2,5-dimethoxyphenyl)sulfamoyl)phenyl)-3-(p-tolylsulfinyl)propanamide (24)

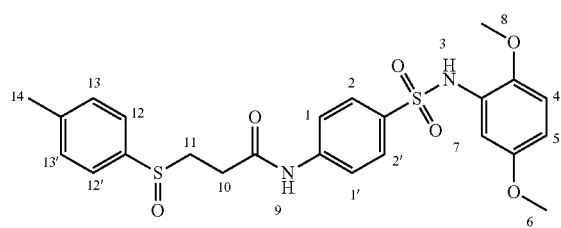

To a solution of N-(4-(N-(2,5-dimethoxyphenyl)sulfamoyl)phenyl)-3-(p-tolylthio)propanamide (2) (300 mg, 0.6 mmol) in EtOH (3 ml) and DCM (2 ml) were successively added H$_2$O$_2$ (30% in water) (0.06 ml, 1.2 mmol) and trifluoromethanesulfonic anhydride (0.102 ml, 0.3 mmol). After stirring over 30 minutes at room temperature, the reaction mixture was quenched by addition of water (5 ml). The aqueous layer was extracted four times with EtOAc (4×5 ml). After drying the combined organic layer with MgSO$_4$, the volatiles were evaporated under vacuum. The crude was purified by chromatography over silica gel (PE/DCM/EtOAc: 50/30/20) affording the expected compound (24) as a white solid (251 mg, 0.51 mmol) with 85% yield. (Rf=0.17 (PE/DCM/EtOAc: 5/3/2); mp=148.1° C.). $^1$H NMR (300 MHz, CDCl$_3$, δ in ppm): 9.66 (s, 1H, N—$H_3$ or N—$H_9$), 7.60 (m, 2H, $H_2$ and $H_{2'}$), 7.57 (m, 2H, $H_1$ and $H_{1'}$), 7.50 (m, 2H, $H_{12}$ and $H_{12'}$), 7.33 (m, 2H, $H_{11}$ and $H_{11'}$), 7.12 (dd, $J_{7-5}$=2.9 Hz, 1H, $H_7$), 7.04 (s, 1H, N—$H_3$ or N—$H_9$), 6.63 (d, $J_{4-5}$=8.9 Hz, 1H, $H_4$), 6.51 (dd, $J_{5-7}$=2.9 Hz, $J_{5-4}$=8.9 Hz, 1H, $H_5$), 3.72 (s, 3H, $H_8$), 3.59 (s, 3H, $H_6$), 3.37 (m, 1H, $H_{11}$), 3.05 (m, 1H, $H_{11}$), 2.97 (m, 1H, $H_{12}$), 2.80 (m, 1H, $H_{12}$), 2.39 (s, 3H, $H_{14}$) $^{13}$C NMR (75 MHz, CDCl$_3$, δ in ppm): 169.07, 154.05, 143.65, 142.77, 142.49, 138.52, 133.69 ($C^{IV}$ Ar), 130.42 ($C_{11}$) 128.57 ($C_2$), 126.83 ($C^{IV}$ Ar), 124.13 ($C_{12}$), 128.75 ($C_2$), 119.09 ($C_1$), 111.68 ($C_4$), 109.84 ($C_5$), 107.17 ($C_7$), 56.38 ($C_8$), 55.90 ($C_6$), 51.40 ($C_{11}$), 30.02 ($C_{12}$), 21.52 ($C_{14}$) MS (EI, m/z): [M$^+$.]=502.6 HRMS: Calculated for [M+H]$^+$: 503.1305; Measured 503.1305. IR (cm$^{-1}$): 3260 (v NH$_{ar}$), 3184 (v=C—H), 1703 (v C=O), 1333 ($v_{as}$ SO$_2$), 716 (v C—S).

Example 29: N-(4-(N-(2,5-dimethoxyphenyl)sulfamoyl)phenyl)-3-tosyl-propanamide (25)

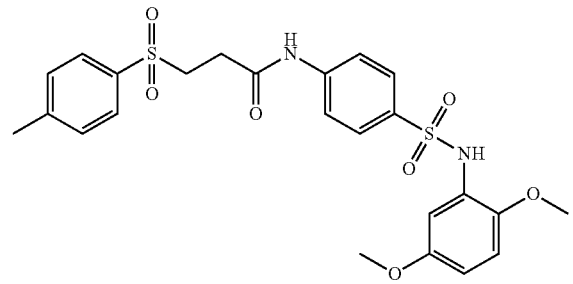

In a 50 mL flask, 3-(toluene-4-sulfonyl)propionic acid (300 mg, 1.3 mmol) was dissolved in dry DCM (10 mL) under argon atmosphere. Oxalyl chloride (1.2 mL, 1.3 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(toluene-4-sulfonyl)propionyl chloride in dry DCM (10 mL) were added dropwise at 0° C. 4-amino-N-(2-methoxyphenyl)benzenesulfonamide (0.4 g, 1.3 mmol) dissolved in 10 mL of dry DCM and Et$_3$N (1 mL, 1.3 mmol). After stirring at room temperature over 48 hours, the reaction mixture was quenched with 5% sodium bicarbonate solution. The aqueous layer was extracted three times with DCM. The combined organic layers were washed successively with a molar solution of HCl, and then with brine. After drying over MgSO$_4$ and removal under vacuum of the solvent, the crude was purified by chromatography over silica gel (EP/DCM/EtOAc (5/3/2)) affording the expected compound (25) as a white solid (0.522 g; 1 mmol) with 77% yield. (Rf=0.10 (PE/DCM/EtOAc: 5/3/2); mp=180.3° C.). $^1$H NMR (400 MHz, DMSO, δ in ppm): 10.33 (s, 1H, N—$H_3$ or N—$H_9$), 7.77 (m, 2H, $H_2$ and $H_{2'}$), 7.65 (m, 2H, $H_{12}$ and $H_{12'}$), 7.58 (m, 2H, $H_{11}$ and $H_{11'}$), 7.42 (m, 2H, $H_1$ and $H_{1'}$), 6.82 (d, $J_{6-5}$=8.9 Hz, 1H, $H_6$), 6.77 (d, $J_{4-5}$=3.1 Hz, 1H, $H_4$), 6.63 (dd, $J_{4-5}$=3.1 Hz, $J_{6-5}$ 1H, $H_5$), 3.63 (s, 3H, $H_7$), 3.56 (t, $J_{9-10}$=7.5 Hz, 2H, $H_9$), 3.48 (s, 3H, $H_8$), 2.68 (t, $J_{9-10}$=7.5 Hz, 2H, $H_9$), 2.34 (s, 3H, $H_{13}$) $^{13}$C NMR (75 MHz, CDCl$_3$, δ in ppm): 167.9, 152.8, 145.7 144.5, 142.4, 135.7 ($C^{IV}$ Ar), 129.8 ($C_1$) 127.8 ($C_2$), 127.8 ($C_{12}$), 118.4 ($C_{11}$), 112.7 ($C_4$), 110.1 ($C_6$), 109.8 ($C_5$), 56.1 ($C_8$), 55.2 ($C_7$), 50.6 ($C_8$), 55.90 ($C_6$), 30.7 ($C_9$), 20.9 ($C_{13}$). HRMS: Calculated for [M+]$^+$: 519.1260; Measured: 519.1263. IR (cm$^{-1}$): 3260 (v NH$_{ar}$), 3184 (v=C—H), 1695 (v C=O), 1506, 1329.5 ($v_{as}$ SO$_2$), 1147.

Example 30: N-(4-(N-(2,5-dimethoxyphenyl)-N-methylsulfamoyl)phenyl)-3-(p-tolylthio)propanamide (26)

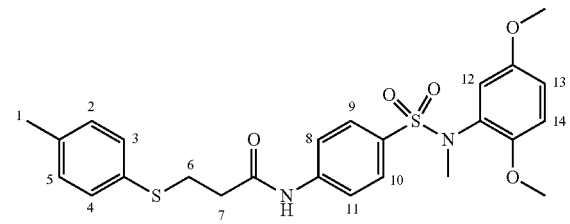

In a 25 mL flask, the 3-(p-tolylthio)propanoic acid (0.55 g, 2.82 mmol) was dissolved in dry DCM (1 mL) under argon atmosphere. Oxalyl chloride (0.24 mL, 2.82 mmol) and DMF (0.03 mL) were successively added to the reaction mixture at 0° C. After 15 minutes of stirring, the apparition of bubbles stopped. Oxalyl chloride and DCM were evaporated under vacuum.

To a solution of this resulting 3-(p-tolylthio)propanoyl-chloride in dry DCM (1 mL) were added dropwise at 0° C. 4-amino-N-(2,5-dimethoxyphenyl)-N'-Methyl-benzenesulfonamide (0.7 g, 2.17 mmol) dissolved in 14 mL of dry DCM and Et$_3$N (0.3 mL, 2.17 mmol). After stirring over 24 hours, the reaction mixture was quenched with brine. The aqueous layer was extracted three times with DCM. The combined organic layers were dried over Na$_2$SO$_4$ and the volatiles were removed under vacuum. The crude was purified by chromatography over silica gel (EP/DCM: 20/80 to 10/90) affording the expected compound (26) (45 mg) as a white solid with 5% yield (Rf: 0.12 (DCM); mp: 48° C.). RMN $^1$H (300 MHz, DMSO-d6): 10.35 (s, 4H, NH), 7.75 (d, 2H, H$^8$-H$^{11}$), 7.58 (d, 2H, H$^9$-H$^{10}$), 7.28 (d, 2H, H$^3$-H$^4$), 7.16 (d, 2H, H$^2$-H$^5$), 6.93 (d, 1H, H$^{14}$), 6.89 (dd, 1H, H$^{13}$), 6.63 (d, 1H, H$^{12}$), 3.66 (CH$_3$), 3.40 (CH$_3$), 3.20 (t, 2H, H$^6$), 3.07 (s, 3H, CH$_3$), 2.67 (t, 2H, H$^7$), 2.27 (s, 3H, H$^1$). RMN $^{13}$C (75 MHz, DMSO-d6): 169.9 (CO), 152.6 (CO), 150.4 (CO), 142.8 (C$^{IV}$), 135.6 (C$^{IV}$), 132.6 (C$^{IV}$), 131.8 (C$^{IV}$), 129.8 (C$_2$-C$_5$), 129.3 (C$^{IV}$), 129.2 (C$_3$-C$_4$), 128.4 (C$_9$-C$_{10}$), 118.5 (C$^8$-C$^{11}$), 116.4 (C$^{12}$), 114.2 (C$^{13}$), 113.2 (C$^{14}$), 55.6 (CH$_3$), 55.5 (CH$_3$), 37.8 (CH$_3$), 36.3 (C$^7$), 28.4 (C$^6$), 20.5 (C$^1$). HRMS: Calculated for [M+]$^+$:501.1518; Measured 501.1518. IR: 3332 (v N—H), 2933 (v Cal-H), 2835 (v OC—H), 1695 (v C=O), 1332 (v$_{as}$SO$_2$), 1308 (Amide III), 1147 (v$_s$ SO$_2$)

Example 31: N-acryloyl-N'-(4-(N-(2,5-dimethoxyphenyl)sulfamoyl)phenyl) Acrylamide (16)

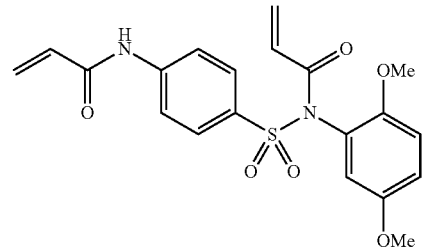 [SMILES: C=CC(=O)Nc1ccc(S(=O)(=O)N(C(=O)C=C)c2cc(OC)ccc2OC)cc1]

To a solution of 4-amino-N-(2,5-dimethoxyphenyl)benzenesulfonamide (0.6 g, 2.00 mmol) in DCM (15 ml) was added successively freshly distilled acryloyl chloride (0.5 mL, 6 mmol) and Et$_3$N (0.84 mL, 6 mmol). After TLC monitoring, the reaction showed full conversion after 48 h of stirring at room temperature. Then, the reaction mixture was quenched by a saturated solution of sodium bicarbonate. After extracting the aqueous layer three times with DCM, the combined organic layers were dried with Na$_2$SO$_4$. After filtration and concentration under vacuum, the crude mixture is obtained as a yellowish oil (0.95 g). The crude was purified by silica gel chromatography using DCM/MeOH as eluent. The expected compound (16) was obtained a white solid (0.810 g, 1.94 mmol) with 97% yield. (Rf: 0.36 (DCM/MeOH: 98/2); mp: 220.8° C.) $^1$H NMR (400 MHz, DMSO, δ in ppm): 10.66 (s, 1H, NH), 8.00 (m, 4H, H$_{arom}$), 7.1 (m, 2H, H$_{arom}$), 7.58 (m, 2H, H$_{11}$ and H$_{11'}$), 7.00 (d, 1H, J$_{4-5}$=2.7 Hz, H$_{arom}$), 6.53 (dd, 1H, J=17.0 Hz, 10.0 Hz, H$_{CH=CH2}$), 6.38 (dd, 1H, J=17.0 Hz, 1.9 Hz, H$_{CH=CH2}$), 6.25 (dd, 1H, J=17.0 Hz, 1.7 Hz, H$_{CH=CH2}$), 5.87 (m, 2H, H$_{CH=CH2}$), 5.74 (dd, 1H, J=10.3 Hz, 1.7 Hz, H$_{CH=CH2}$), 3.82 (s, 3H, OMe), 3.71 (s, 3H, OMe). $^{13}$C NMR (100.6 MHz, DMSO, δ in ppm): 164.2; 163.7; 153.1; 150.3; 143.9; 132.6; 131.5; 131.4; 130.4; 128.2; 127.8; 124.0; 118.5; 117.3; 116.7; 113.4; 56.0; 55.7. HRMS: Calculated for [M+]$^+$: 417.1120; Measured: 417.1123. IR (cm$^{-1}$): 3337 (v N—H), 2920 (v Cal-H), 1696, 1664, 1614, 1507, 1403, 1355, 1160.

Activity Results

| | Name | Relative activity (NSC23766) | IC$_{50}$ |
|---|---|---|---|
| | NSC23766 | — | $10$-$50 \cdot 10^{-6}$ M |
| Chemical structure | | | |
| (structure 1) | (1) | > | $3 \cdot 10^{-8}$ M |
| (structure 2) | (2) | > | $10^{-9}$ M |

| | Name NSC23766 | Relative activity (NSC23766) — | IC$_{50}$ 10-50•10$^{-6}$ M |
|---|---|---|---|
| 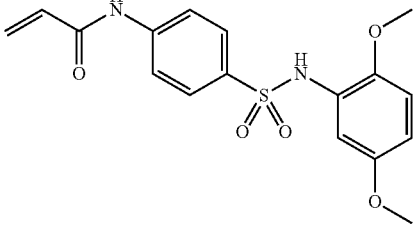 | (3) | > | 10$^{-10}$M |
| 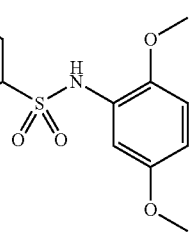 | (6) | > | 10$^{-9}$M |
| 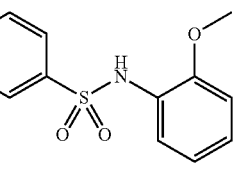 | (17) | > | 10$^{-9}$M |
| 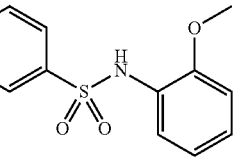 | (18) | > | 10$^{-9}$M |
| 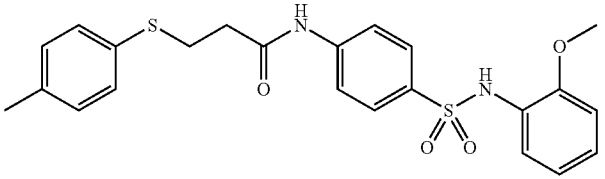 | (19) | > | 10$^{-9}$M |
| 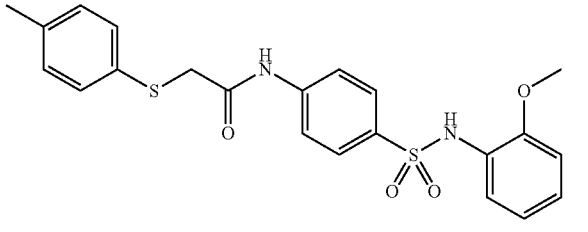 | (20) | > | 10$^{-9}$M |
| 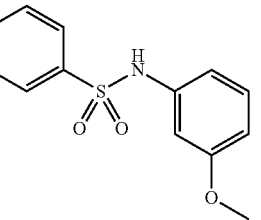 | (22) | > | 10$^{-9}$M |

FIGURES

Figure 2:
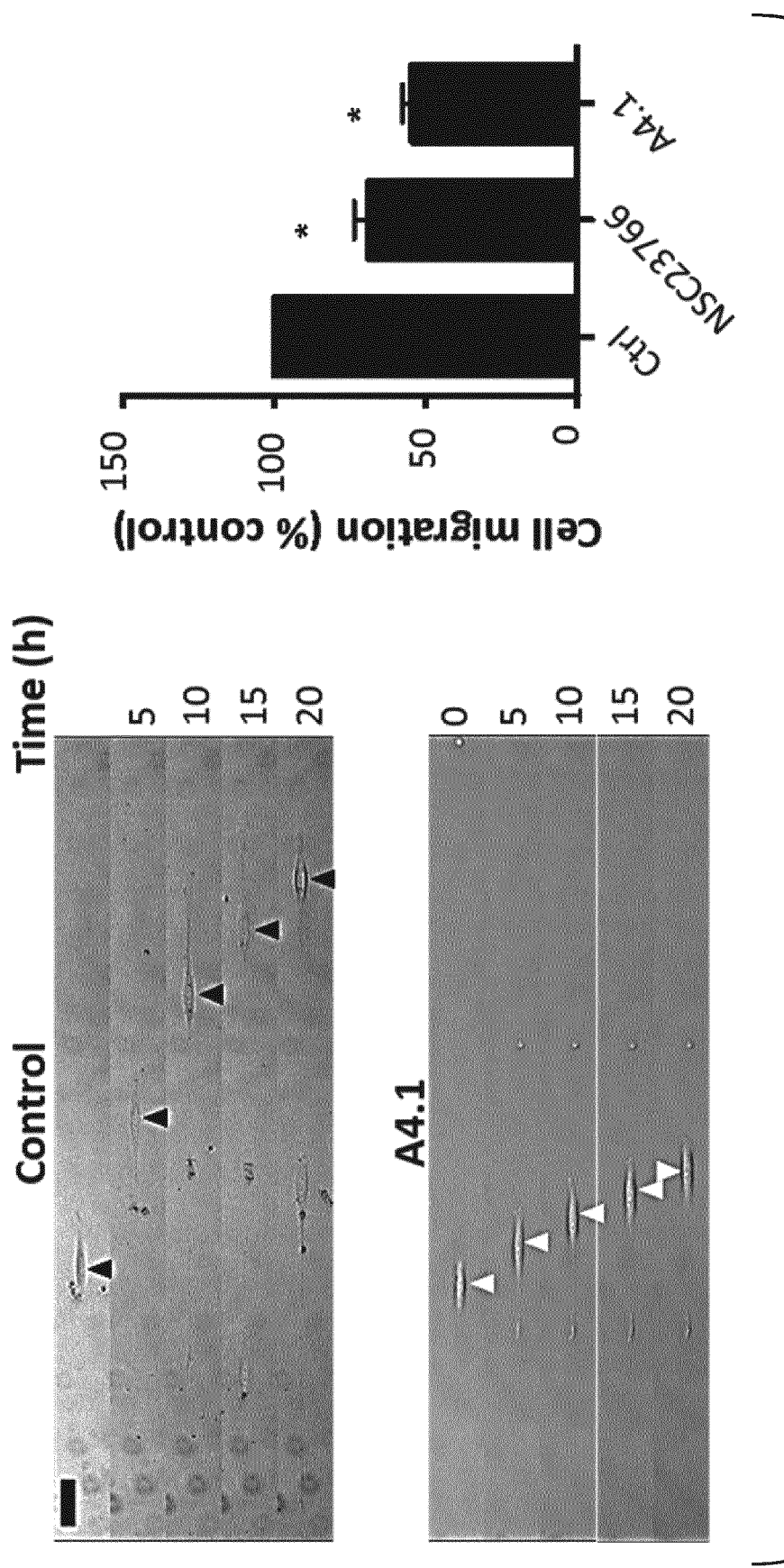
Figure 3:
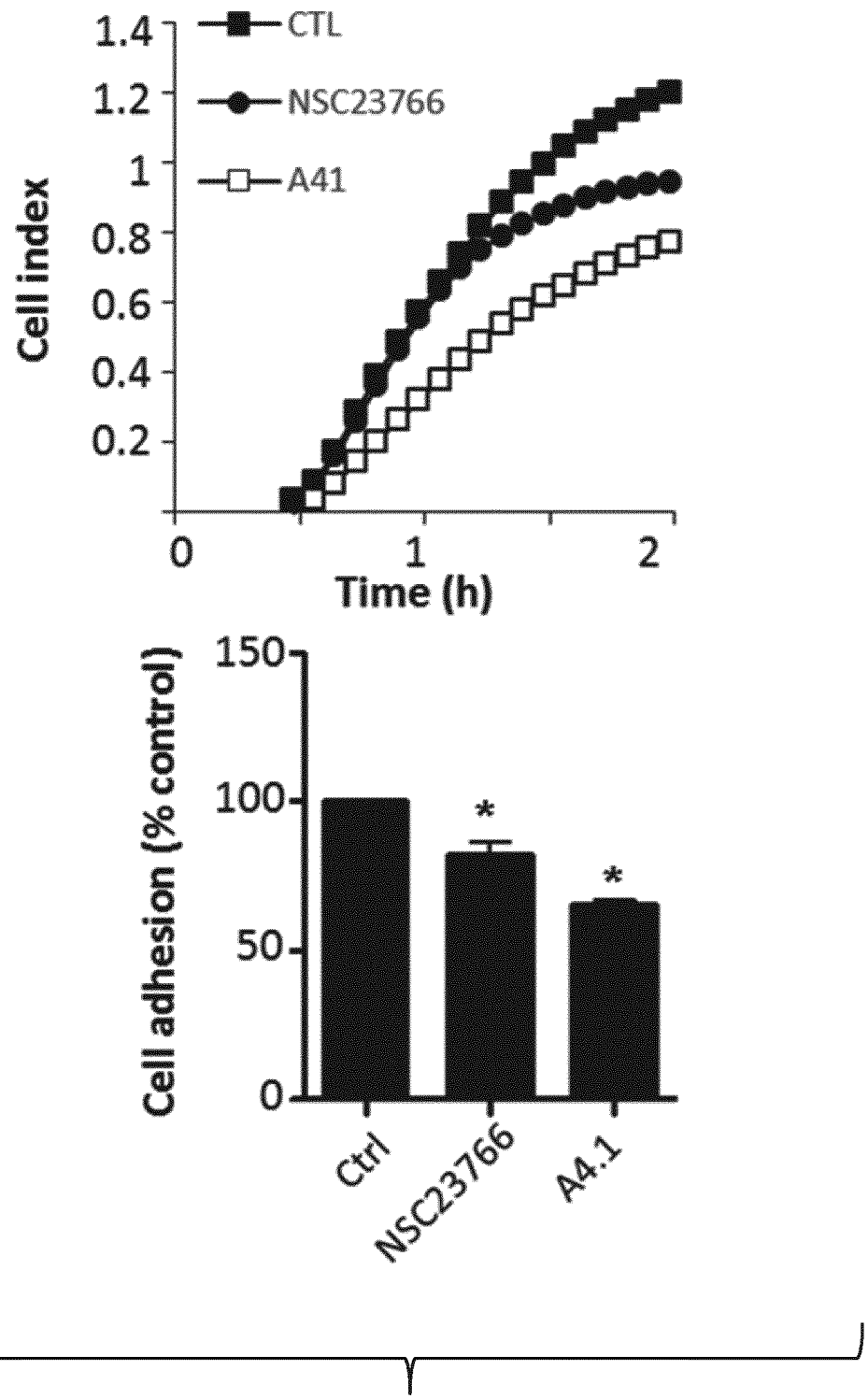

FIGS. 1 to 3 relate to the inhibition of the Rac-induced cell functions by compound (2) (or A4.1). FIG. 1: A4.1 (or (2)) blocks Rac activator-induced actin reorganization. 3T3 cells were incubated in serum-free growth medium, either alone, or supplemented with (2) or NSC23766 at indicated concentration 1 h before Rac activation. Ruffles are indicated by arrows (left panel). Percentages of cells with ruffles were quantified (right panel). Results shown are representative of 3 independent experiments. FIG. 2: (2) decreases cell migration. 3T3 cells were incubated or not with (2) or NSC23766. Left panel, representative records with arrows indicating the cell location at different times. Right panel, quantification of cell speed in each experimental conditions. Results shown are representative of 2 independent experiments. FIG. 3: (2) decreases cell adhesion. Upper panel, representative kinetics of fibroblast adhesion pre-treated or not with 10 μm (2) or NSC23766. Lower panel, quantification of cell adhesion. Results shown are representative of 3 independent experiments.

Figure 4:
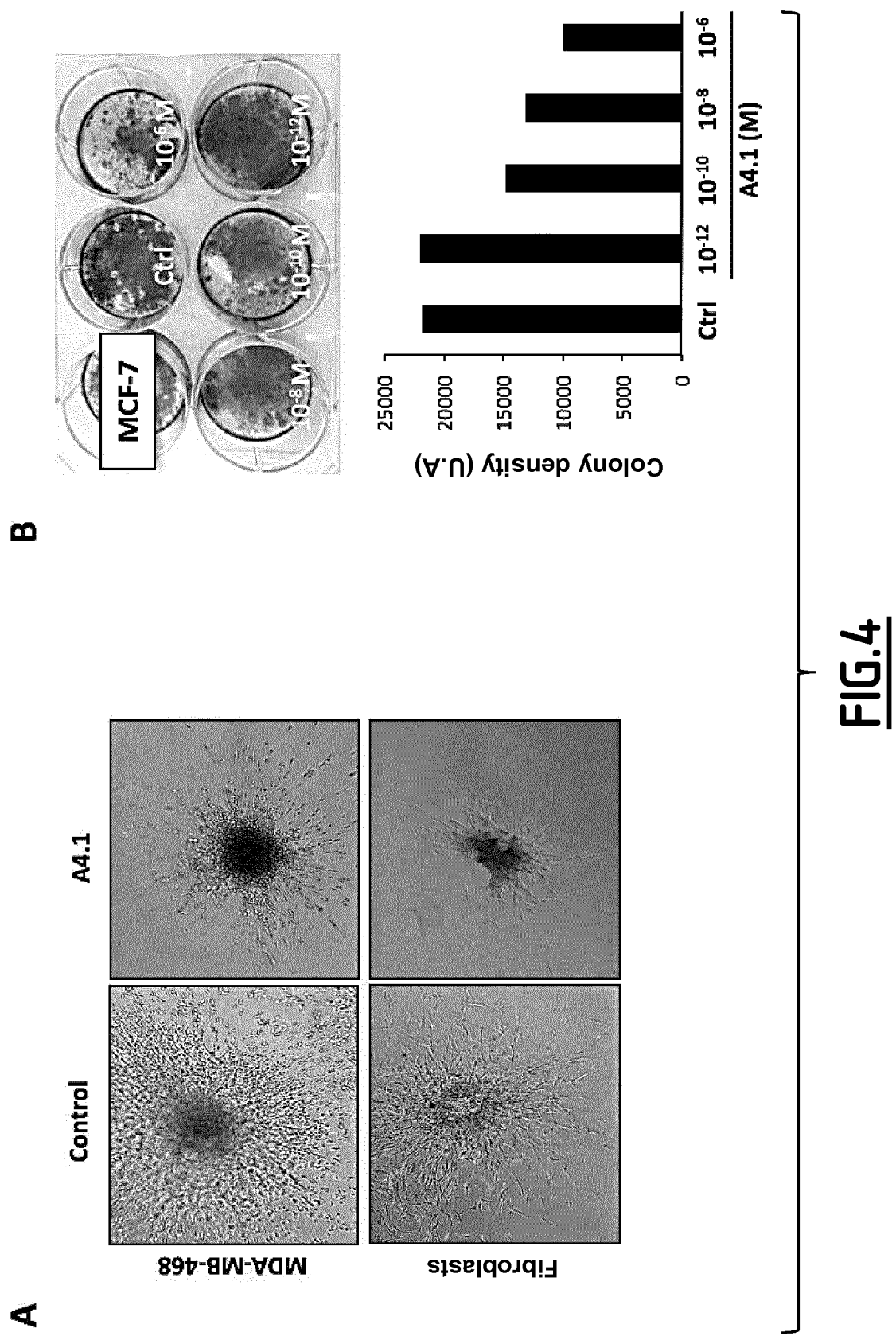

FIG. 4 relates to the inhibition of the Rac-dependent cell functions involved in cancer cells by (2). FIG. 4A: Breast cancer cell line MDA-MB-468 and primary human fibroblast from breast cancer tumors were seeded in 3D-gel containing or not (2). Cell invasion was observed after 72 h (n=3 independent experiments). FIG. 4B: Effect of (2) on foci assay.

Figure 5:
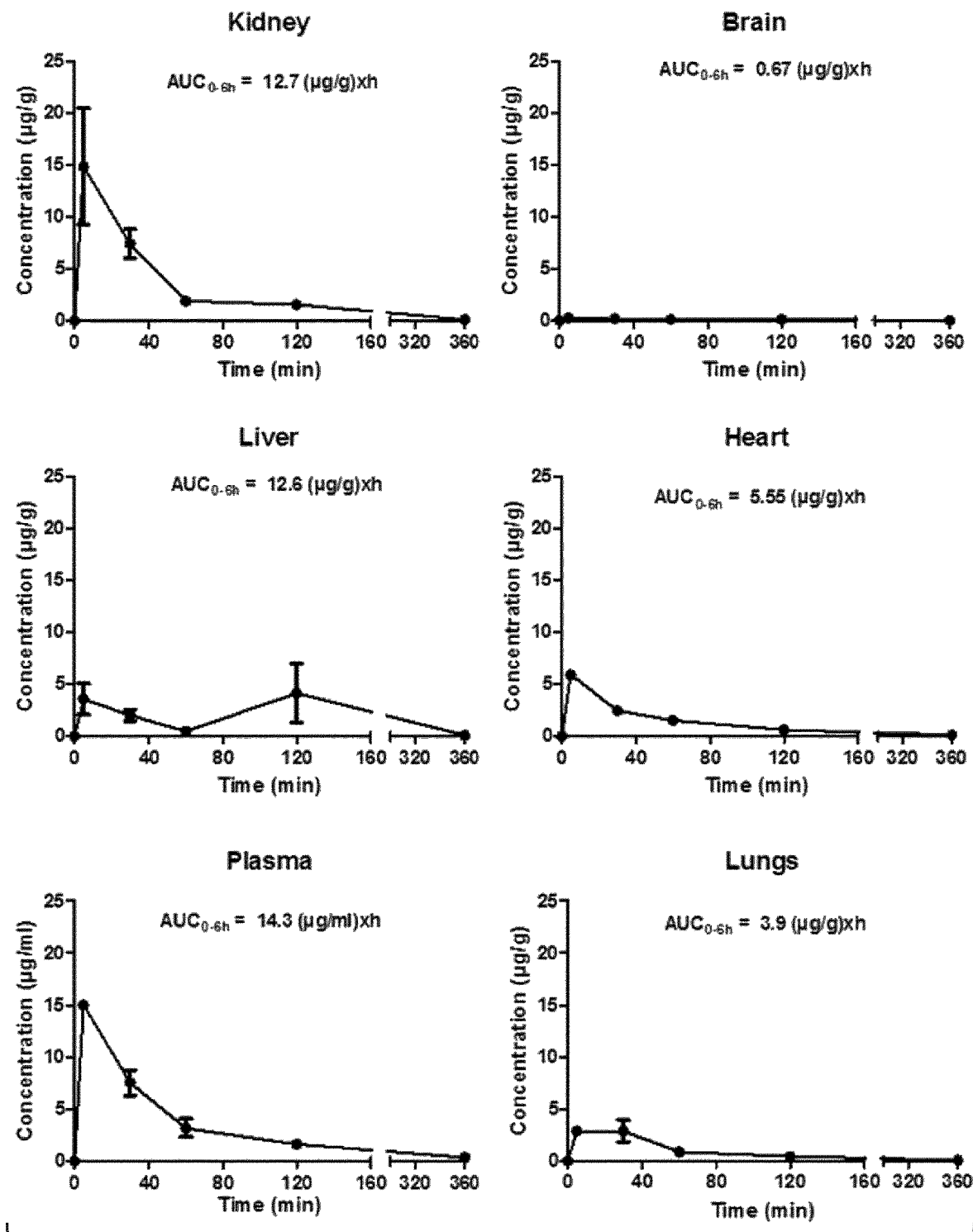

FIG. 5 relates to the pharmacokinetics of compound (2) by analyzing kidney, brain, liver, heart, plasma samples, and lungs from male C57BL6 adult mice after intraperitonal injection. The curves of this Figure represent the concentration in μg/g over time in minutes.

Figure 6:
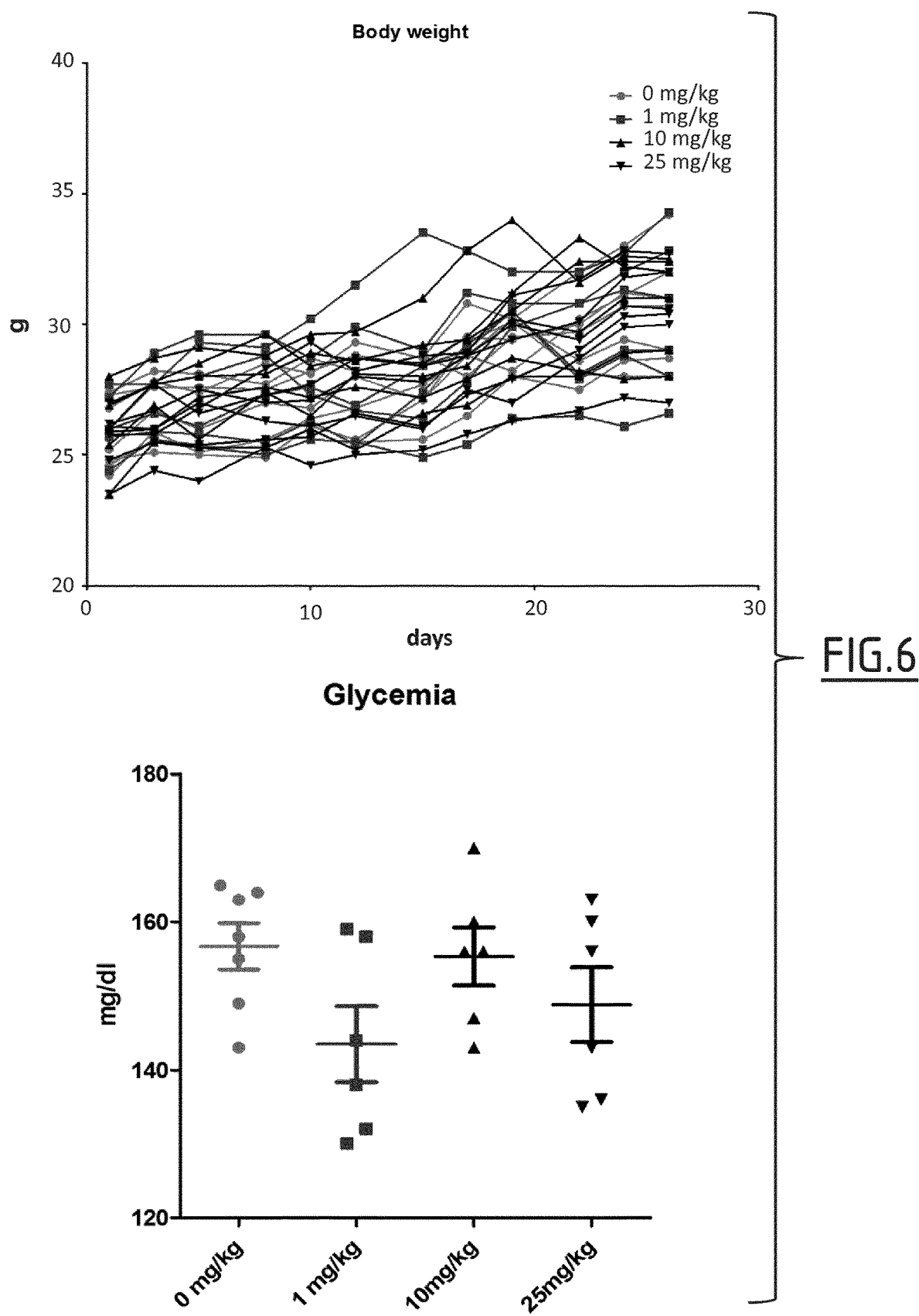
Figure 7:
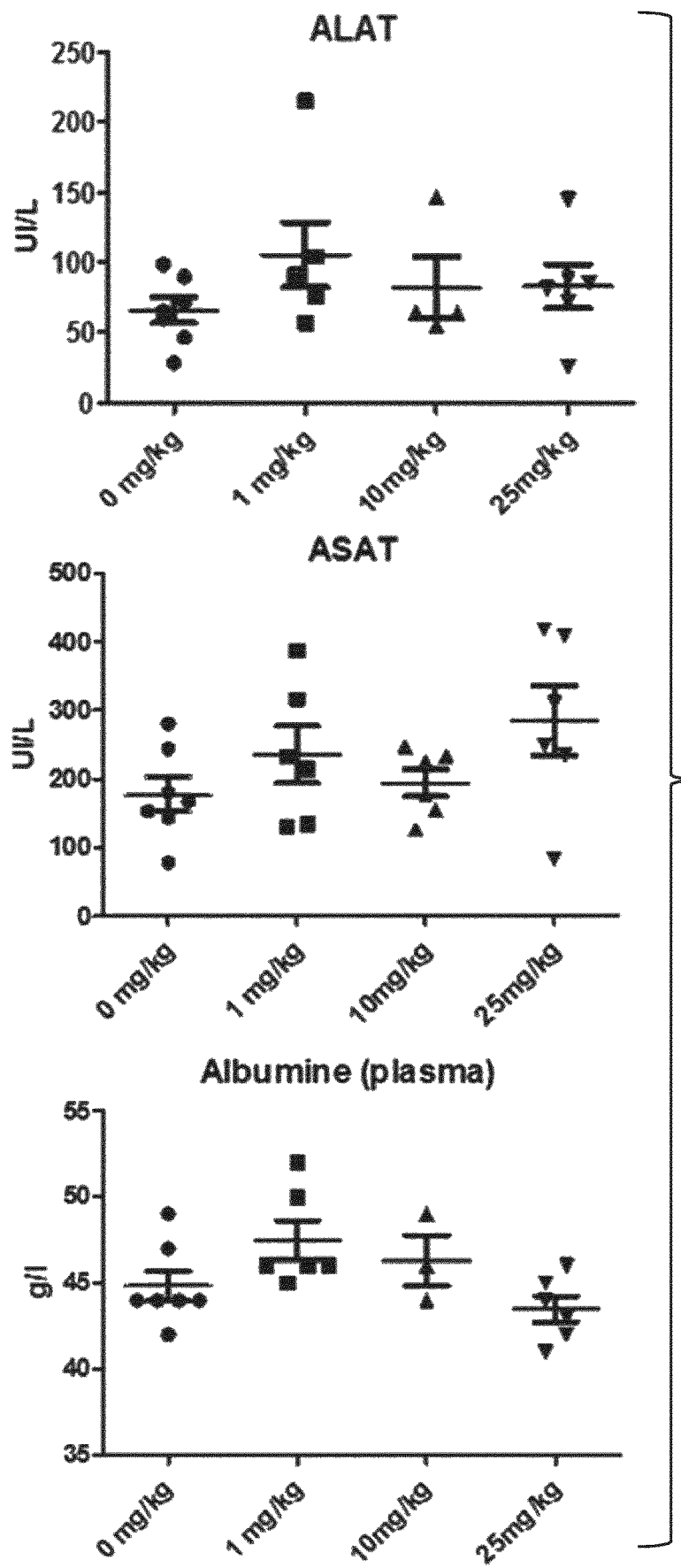
Figure 8:
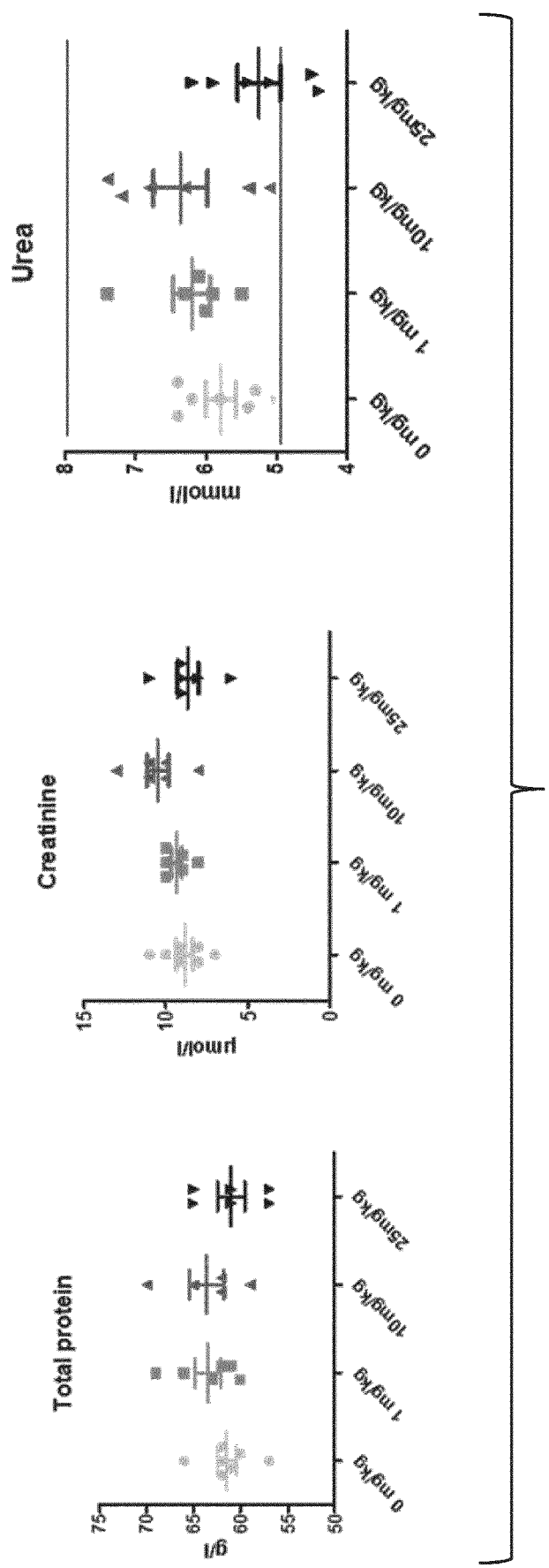

FIGS. 6 to 8 relate to the effect of chronic IP injections of compound (2) on physiological parameters: body weight, glycemia, hepatic and renal functions.

Figure 9:
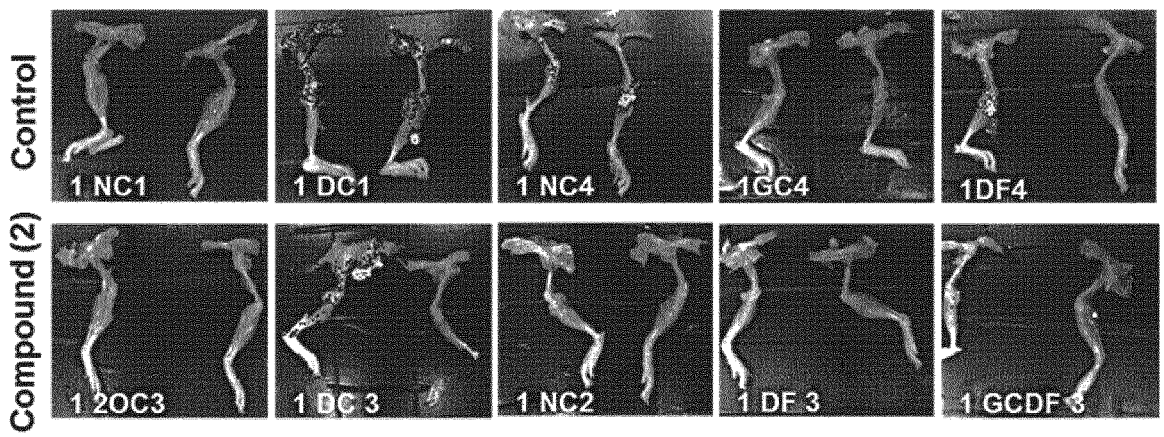
Figure 9:
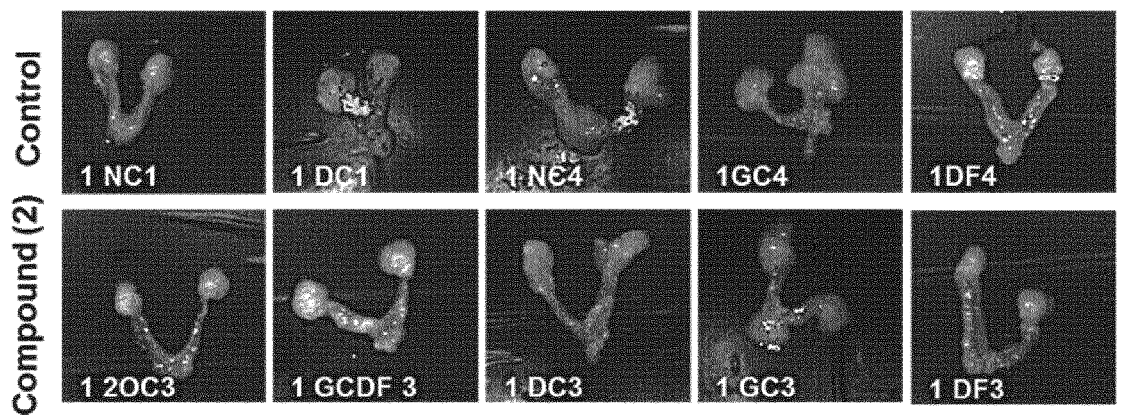
Figure 9:
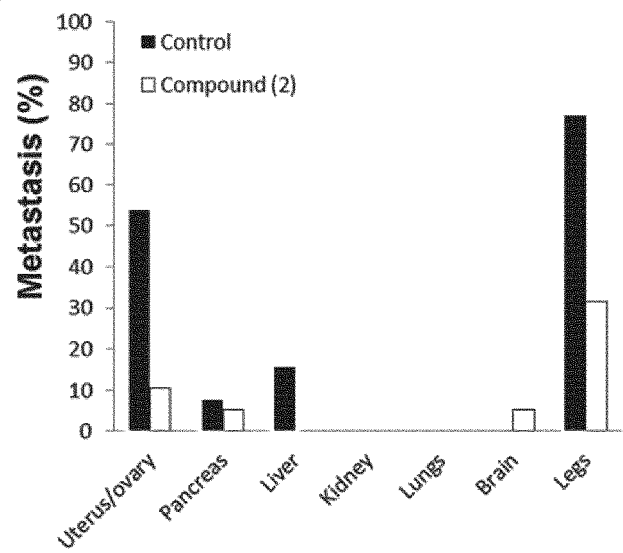

FIG. 9 relates to the in vivo efficiency of compound (2) to inhibit metastasis in a xenograft mouse tumor model using MDA-MB-468 (Luciferase+) cell line in 5-week-old NMRI mice.

Biology Results
Materials and Methods
Cell Culture, Transfection and Actin Staining.

NIH3T3, MCF-7 and MDA-MB-468 cells grew up in DMEM (Gibco; Invitrogen) containing 10% foetal bovine serum, 100 units/mL penicillin and 100 μg/mL streptomycin at 37° C. and 5% $CO_2$. The culture medium was changed every 72 hours.

cDNA coding for constitutive active Rac1 ($Rac^{V12}$-RFP) were transfected in NIH3T3 with jetPEI (Polyplus transfection) according to the manufacturer's instructions. After treatments, fibroblasts were fixed with 4% paraformaldehyde in PBS, permeabilized in PBS 0.5% Triton X-100, and incubated with 130 μg/mL of FITC-conjugated phalloidin (Sigma) to visualize F-actin. After staining, images were captured by a fluorescence microscope (Nikon). The actin cytoskeleton organization was analyzed to observe Rac1-dependent ruffle formation.

Analysis of Rac1 Activity.

In NIH3T3 cells lysates, Rac1 activity was evaluated by active Rac immunoprecipitation using anti-Rac-GTP antibody (26903, NewEast Biosciences). The precipitated active Rac was subjected to SDS-PAGE and detected by immunoblot with anti-Rac1 antibody (BD biosciences).

Unidirectional Cell Migration.

Cells (1000/well) were seeded in a 96 well plate with 10 mm fibronectin stripes (CytooPlates Motility, CYTOO) in medium with 1% SVF and allowed to spread for 4 hours before capturing time-lapse images for 24 hours (image/10 minutes) on a Widefield Leica DMI 6000B drove with Metamorph software. Cells speed was measured with ImageJ software.

Cell Adhesion Assay Using Impedance Technology.

Cells (10000/well) were seeded in a 96 well plate microtiter xCELLigence assay plate (E-Plate) (ACEA Biosciences Inc.) and placed on the Real-time xCELLigence Cell Analyzer (Roche Applied Science) platform at 37° C. to measure the "cell index" every 5 min for a period of 6 hours. The cell index unit is defined as $(R_n-R_b)/15$. $R_n$ is the cell electrode impedance of the well when it contains cells. $R_b$ is the background impedance of the well with the media alone.

Transformation Analyses.

For primary focus formation assays, MCF-7 cells were plated at a density of $10^5$ cells/well of a 6-well plate. Cells were allowed to reach confluency and were maintained on complete growth medium supplemented with indicated concentration of A4.1 (or compound (2)) or vehicle until focus formation occurred. Foci of transformed cells was quantitated after 21 days.

Statistics.

All data are expressed as the mean±SEM of sample size n. For multiple comparisons, the non-parametric Kruskal-Wallis test was used followed by Dunns' post-test. For individual comparisons, statistical analysis was performed using non-parametric t-test (Mann-Whitney). Data analysis was performed using the GraphPad Prism software. The threshold for statistical significance was set at P<0.05.

Results

Compound (2) Inhibits Rac-Dependent Cell Functions Involved in Oncogenesis

The small GTPase Rac is extensively described to play a crucial role in actin cytoskeleton organization, cell adhesion and migration. To evaluate the ability of A4.1 to inhibit Rac-mediated cell functions, the actin structures of the cells stimulated by Rac activator was examined in the presence or absence of A4.1 (or compound (2)). Rac activator stimulated membrane ruffling in fibroblasts (FIG. 1A). However, in the presence of (2) or NSC23766, the efficiency of Rac activator to induce ruffle is strongly decreased. Interestingly, the dose-dependent inhibition observed in fibroblasts suggest that the small molecule (2) ($IC_{50}$=0.67 nM) is a powerful Rac inhibitor compared to NSC23766 ($IC_{50}$=2.6 μM). This hypothesis is reinforced by the cell migration (FIG. 1B) and adhesion (FIG. 1C) assays. Indeed, NSC23766 and (2) slow down cell migration and adhesion, however a higher inhibition is always recorded with cells treated with the compound (2).

Compound (2) Inhibits Rac-Dependent Cell Functions Involved in Cancer Cells

Rac1 over activity is implicated in various steps of oncogenesis including initiation, progression, invasion, and metastasis. The ability of (2) to inhibit a constitutive active mutant of Rac1, $Rac^{V12}$ was evaluated. In control condition, expression of RFP-$Rac^{V12}$ in fibroblasts induces changes in actin cytoskeleton leading to ruffles formation (data not shown). This effect is prevented by (2) (10 μM). In addition, it was observed that (2) limits the location of $Rac^{V12}$ at the plasma membrane, essential to initiate ruffles formation. These results demonstrate that the lead molecule (2) could inhibit oncogenic Rac1 over activity and cell functions associated.

To confirm this hypothesis, cancer cells invasion was analyzed in 3D gel. The breast cancer cell line MDA-MB-468 or primary fibroblasts from human breast cancer were seeded in gels containing or not (2) (10 μM). After 48 h, it was observed that A4.1 strongly decreased (>50%) cell invasion compared to control condition (FIG. 2A). These results suggest that (2) should limit cancer cells invasion and consequently metastasis formation.

Compound (2) Inhibits Focus Formation of Breast Cancer Cells

Malignant transformation of cells is typically associated with increased proliferation, loss of contact inhibition, acquisition of anchorage-independent growth potential, and the ability to form foci in culture cells. A focus formation assay was used to test whether (2) affects the clonogenic potential of breast cancer cells MCF-7. After 3 weeks of treatments, the cells's foci were fixed, stained and counted (FIG. 2B). It was observed that MCF-7 cells treated with (2) exhibited smaller focus diameter as well as focus numbers compared with control cells ($IC_{50}$=2.3 nM). These data indicated that (2) significantly decreases the cells' focus formation potential, which correlates with the formation of tumors in vivo.

In Mice, Compound (2) Prevents Triple-Negative Breast Cancer Metastasis.

To test whether compound (2) would have an acceptable therapeutic index in vivo, the pharmacokinetics of compound (2) were measured by analyzing plasma samples, brain, heart, kidney, liver and lungs from male C57BL6 adult mice after intraperitonal injection (IP) (FIG. 5). In addition, we evaluated the effect of chronic (daily during 4 weeks) IP injections of compound (2) on physiological parameters: body weight, glycemia, hepatic and renal functions (FIGS. 6 to 8). These analyses demonstrated 81.5% of bioavailability of compound (2) by IP route and no major side effects after chronic injection of compound (2) at 25 mg/kg (FIGS. 6 to 8). These results demonstrate suitable properties of compound (2) to be used daily in vivo at 25 mg/kg and could be tested in a murine triple-negative breast cancer model.

The in vivo efficiency of compound (2) to inhibit metastasis was evaluated in a xenograft mouse tumor model using MDA-MB-468 (Luciferase+) cell line in 5-week-old NMRI mice. When the tumor volume reached 1,000 mm³, exeresis of the primary tumor was done to monitor predominantly metastasis initiation and progression. Compound (2) was administered everyday via intraperitoneal injection (25 mg/kg/d) during 4 weeks. Then, xenografted mice were sacrified and organs were imaged (FIGS. 9A and 9B). We observed that compound (2) decreases significantly bone, hepatic, uterine and ovarian metastases (FIG. 9C). These results suggest that inhibition of Rac by IP injection of compound (2) would be a new therapeutic approach to prevent metastasis initiation and invasion in aggressive cancers.

The invention claimed is:

1. A method for the treatment of cancer, comprising administering to a mammal in need thereof a therapeutically effective amount of a compound having the following formula (VII):

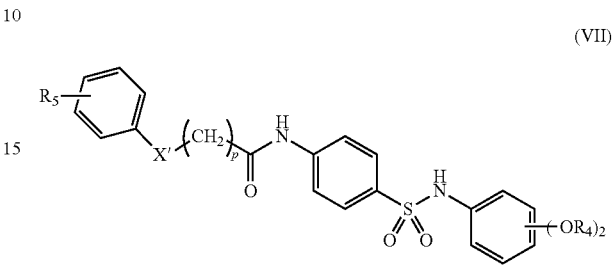

(VII)

wherein:
p is an integer from 1 to 3 inclusive;
X' is chosen from the group consisting of: —S—, —NH—, —NR$_d$—, —CH$_2$—, —SO$_2$—, and —SO—, R$_d$ being H or a (C$_1$-C$_6$)alkyl group;
R$_5$ is a (C$_1$-C$_6$)alkyl group; and
the R$_4$ groups, identical or different, are chosen from the (C$_1$-C$_6$)alkyl groups.

2. The method of claim 1, wherein X' is —CH$_2$— or —S—.

3. The method of claim 1, wherein the compound of formula (VII) is the following compound:

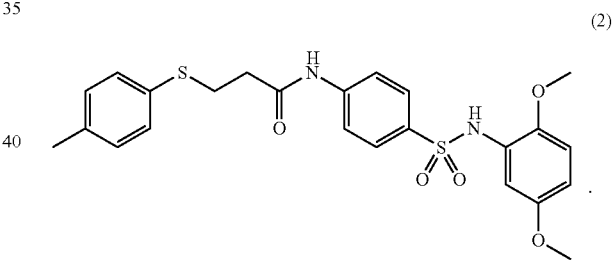

(2)

4. (Allowed) The method of claim 1, wherein the cancer is breast cancer.

* * * * *